(12) United States Patent
Horwitz

(10) Patent No.: US 8,318,162 B2
(45) Date of Patent: Nov. 27, 2012

(54) ANTIBODIES TO HIGH MOLECULAR WEIGHT MELANOMA ASSOCIATED ANTIGEN

(75) Inventor: Arnold H. Horwitz, Berkeley, CA (US)

(73) Assignee: Xoma Technology Ltd., Berkeley, CA (US)

( * ) Notice: Subject to any disclaimer, the term of this patent is extended or adjusted under 35 U.S.C. 154(b) by 0 days.

(21) Appl. No.: 13/384,197

(22) PCT Filed: Jul. 16, 2010

(86) PCT No.: PCT/US2010/042347
§ 371 (c)(1),
(2), (4) Date: Mar. 21, 2012

(87) PCT Pub. No.: WO2011/009090
PCT Pub. Date: Jan. 20, 2011

(65) Prior Publication Data
US 2012/0171226 A1 Jul. 5, 2012

Related U.S. Application Data

(60) Provisional application No. 61/226,166, filed on Jul. 16, 2009.

(51) Int. Cl.
*A61K 39/395* (2006.01)
*A61K 39/00* (2006.01)
*G01N 33/53* (2006.01)
*C07K 16/28* (2006.01)
*C12P 21/08* (2006.01)

(52) U.S. Cl. ............... 424/130.1; 424/133.1; 424/155.1; 424/178.1; 435/7.1; 435/975; 530/387.1; 530/387.3; 530/388.8; 530/391.3

(58) Field of Classification Search .................. None
See application file for complete search history.

(56) References Cited

U.S. PATENT DOCUMENTS

| | | | |
|---|---|---|---|
| 4,590,071 A * | 5/1986 | Scannon et al. | 424/183.1 |
| 4,970,303 A | 11/1990 | Reardon et al. | |
| 5,766,886 A * | 6/1998 | Studnicka et al. | 435/70.21 |
| 7,517,967 B2 * | 4/2009 | Chatterjee et al. | 530/388.8 |
| 2003/0118592 A1 * | 6/2003 | Ledbetter et al. | 424/178.1 |
| 2003/0203447 A1 * | 10/2003 | Horwitz | 435/69.1 |
| 2004/0110933 A1 * | 6/2004 | Rondon et al. | 530/388.22 |
| 2007/0202593 A1 * | 8/2007 | Liu et al. | 435/325 |
| 2007/0212361 A1 | 9/2007 | Ferrone | |
| 2011/0200608 A1 * | 8/2011 | Wang et al. | 424/142.1 |

FOREIGN PATENT DOCUMENTS

| | | |
|---|---|---|
| EP | 0074279 B1 | 8/1987 |
| WO | 0126672 A1 | 4/2001 |
| WO | 2006032127 A1 | 3/2006 |
| WO | 2006100582 A1 | 9/2006 |
| WO | 2007009191 A1 | 1/2007 |
| WO | 2007109193 A2 | 9/2007 |
| WO | 2008030625 A2 | 3/2008 |
| WO | 2008121125 A1 | 10/2008 |
| WO | 2010033866 A2 | 3/2010 |
| WO | 2010045495 A2 | 4/2010 |
| WO | 2011009090 A1 | 1/2011 |

OTHER PUBLICATIONS

Campoli et al. Human high molecular weight-melanoma-associated antigen (HMW-MAA): a melanoma cell surface chondroitin sulfate proteoglycan (MSCP) with biological and clinical significance. Crit Rev Immunol (2004) 24:267-96.
Chekenya, et al. The NG2 chondroitin sulfate proteoglycan: role in malignant progression of human brain tumours. Int J Dev Neurosci (1999) 17:421-35.
Eisenmann, et al. Melanoma chondroitin sulphate proteoglycan regulates cell spreading through Cdc42, Ack-1 and p130cas. Nat Cell Biol (1999) 1:507-13.
Gonzalez, et al., Single-dose murine monoclonal antibody ricin A chain immunotoxin in the treatment of metastatic melanoma: a phase I trial. Mol Biother. (1991) 3(4):192-6.
Harkonen, et al., Toxicity and Immunogenicity of Monoclonal Antimelanoma Antibody-Ricin A Chain Immunotoxin in Rats. Cancer Research (1987) 47:1377-1382.
Hertler, et al., Humoral immune response to a ricin A chain immunotoxin in patients with metastatic melanoma. Cancer Drug Deliv. (1987) 4(4):245-53.
Iida, et al. Melanoma chondroitin sulfate proteoglycan regulates matrix metalloproteinase-dependent human melanoma invasion into type I collagen. J. Biol Chem (2001) 276:18786-94.
Kageshita, et al. Immunohistochemical analysis of antimelanoma monoclonal antibodies, with special reference to fetal tissue distribution J. Invest. Dermatol. (1985) 85: 535-37.
Mischak, et al., Human antibody responses to components of the monoclonal antimelanoma antibody ricin A chain immunotoxin XomaZyme-MEL. Mol Biother. (1990) 2(2):104-9.
Selvaggi, et al., Phase I/II study of murine monoclonal antibody-ricin A chain (XOMAZYME-Mel) immunoconjugate plus cyclosporine A in patients with metastatic melanoma. J Immunother Emphasis Tumor Immunol. (1993) 13(3):201-7.
Spitler, et al., Therapy of patients with malignant melanoma using a monoclonal antimelanoma antibody-ricin A chain immunotoxin. Cancer Res. (1987) 47(6):1717-23.
Wagner, et al., Reduction of Human Melanoma Tumor Growth in Severe Combined Immunodeficient Mice by Passive Transfer of Antibodies Induced by a High Molecular Weight Melanoma-Associated Antigen Mimotope Vaccine. Clin Cancer Res (2008) 14(24): 8178-8183.
Yang, et al. Melanoma chondroitin sulfate proteoglycan enhances FAK and ERK activation by distinct mechanisms. J Cell Biol (2004) 165:881-91.
Yang, et al., Melanoma Proteoglycan Modifies Gene Expression to Stimulate Tumor Cell Motility, Growth, and Epithelial-to-Mesenchymal Transition. Cancer Res (2009) 69: (19): 7538-7547.

* cited by examiner

*Primary Examiner* — Phuong Huynh
(74) *Attorney, Agent, or Firm* — Diane Wilcock; K&L Gates LLP

(57) ABSTRACT

The present disclosure relates to anti-high molecular weight melanoma associated antigen (HMW-MAA) antibodies which bind to human HMW-MAA. Such antibodies may be used to treat diseases or disorders characterized by expression of HMW-MAA including cancer, for example, melanoma, basal cell carcinoma, ALL or AML.

10 Claims, 2 Drawing Sheets

ANTIBODIES TO HIGH MOLECULAR WEIGHT MELANOMA ASSOCIATED ANTIGEN

CROSS-REFERENCE TO RELATED APPLICATIONS

This application claims priority to U.S. Provisional Patent Application No. 61/226,166, filed on Jul. 16, 2009; and International Patent Application No. PCT/US2010/042347, filed on Jul. 16, 2010, each of which is hereby incorporated by reference in its entirety.

FIELD

The present disclosure relates to anti-high molecular weight melanoma associated antigen (HMW-MAA) antibodies which bind with high affinity to human HMW-MAA. Antibodies may comprise a light chain variable region comprising the amino acid sequence of SEQ ID NO: 8 or SEQ ID NO: 9 and a heavy chain variable region comprising the amino acid sequence of SEQ ID NO: 11 or SEQ ID NO 12. Antibodies may alternatively comprise a light chain variable region comprising the amino acid sequence of SEQ ID NO: 2 or SEQ ID NO: 3 and a heavy chain variable region comprising the amino acid sequence of SEQ ID NO: 5 or SEQ ID NO 6. Antibodies that have been human-engineered as described herein may be used to treat diseases or disorders characterized by expression of HMW-MAA including cancer, for example, melanoma, basal cell carcinoma, ALL or AML.

BACKGROUND

The high molecular weight melanoma-associated antigen (HMW-MAA) is a 450 kD chondroitin sulfate proteoglycan with a 250 kD core glycoprotein. HMW-MAA consists of a large extracellular domain which contains fifteen potential N-linked glycosylation sites, a hydrophobic transmembrane region and a short cytoplasmic tail of seventy-five amino acids which contains a potential protein kinase C phosphorylation site. This antigen, also known as chondroitin sulfate proteoglycan 4 (CSPG4) and melanoma-associated chondroitin sulfate proteoglycan (MCSP), belongs to a family of adhesion receptors that mediate both cell-cell and cell-extracellular matrix interactions (Chekenya et al. (1999) *Int J Dev Neurosci* 17:421-35).

HMW-MAA is not expressed on normal human tissues except for nevus cells, pericytes and vascular endothelial cells. The expression of HMW-MAA on vascular endothelial cells suggests a possible role in angiogenesis. Notably, HMW-MAA is expressed on the majority of melanoma cells and on the surface of hematopoeitic progenitor cells in acute lymphocytic leukemia (ALL) and acute myelogenous leukemia (AML) (Campoli et al. (2004) *Crit Rev Immunol* 24:267-96) as well as on basal cell carcinoma cells (Kageshita (1985) *J. Invest. Dermatol.* 85: 535-37). HWM-MAA may be shed from a cell and is detectable in the sera of both melanoma patients and normal individuals.

Several lines of evidence suggest that HMW-MAA plays important roles in intracellular signal cascades important for cellular adhesion, spreading, and invasion. These include the activation of small Rho family GTPase Cdc42 and of the adaptor protein p130cas, as well as the association of HMW-MAA with membrane-type 3 matrix metalloproteinase on melanoma cells (Eisenmann at al. (1999) *Nat Cell Biol* 1:507-13; Iida et al. (2001) *J. Biol Chem* 276:18786-94). Furthermore, elevated HMW-MAA expression in early tumors has been proposed to facilitate tumor progression by enhancing the activation of focal adhesion kinase (FAK) and extracellular signal-regulated protein kinases 1 and 2 (ERK1/2) (Yang et al. (2004) *J Cell Biol* 165:881-91), Accordingly, HMW-MAA may be a target in the treatment of cancer.

SUMMARY

The present disclosure relates to antibodies that bind to high molecular weight melanoma associated antigen (HMW-MAA).

The present disclosure provides anti-HMW-MAA antibodies which bind with high affinity to human HMW-MAA comprising a light chain variable region comprising the amino acid sequence of SEQ ID NO: 8 or SEQ ID NO: 9 and a heavy chain variable region comprising the amino acid sequence of SEQ ID NO: 11 or SEQ ID NO 12.

In preferred embodiments, the anti-HMW-MAA antibodies comprise a light chain variable region that comprises the amino acid sequence of SEQ ID NO: 8 and a heavy chain variable region that comprises the amino acid sequence of SEQ ID NO: 11. In some embodiments, the anti-HMW-MAA antibodies comprise a light chain variable region that comprises the amino acid sequence of SEQ ID NO: 8 and a heavy chain variable region that comprises the amino acid sequence of SEQ ID NO: 12. In preferred embodiments, the anti-HMW-MAA antibodies comprise a light chain variable region that comprises the amino acid sequence of SEQ ID NO: 9 and a heavy chain variable region that comprises the amino acid sequence of SEQ ID NO: 11. In preferred embodiments, the anti-HMW-MAA antibodies comprise a light chain variable region that comprises the amino acid sequence of SEQ ID NO: 9 and a heavy chain variable region that comprises the amino acid sequence of SEQ ID NO: 12.

The present disclosure also provides anti-HMW-MAA antibodies which bind with high affinity to human HMW-MAA comprising a light chain variable region comprising the amino acid sequence of SEQ ID NO: 2 or SEQ ID NO: 3 and a heavy chain variable region comprising the amino acid sequence of SEQ ID NO: 5 or SEQ ID NO 6. In preferred embodiments, the anti-HMW-MAA antibodies comprise a light chain variable region that comprises the amino acid sequence of SEQ ID NO: 2 and a heavy chain variable region that comprises the amino acid sequence of SEQ ID NO: 5. In some embodiments, the anti-HMW-MAA antibodies comprise a light chain variable region that comprises the amino acid sequence of SEQ ID NO: 2 and a heavy chain variable region that comprises the amino acid sequence of SEQ ID NO: 6. In some embodiments, the anti-HMW-MAA antibodies comprise a light chain variable region that comprises the amino acid sequence of SEQ ID NO: 3 and a heavy chain variable region that comprises the amino acid sequence of SEQ ID NO: 5. In some embodiments, the anti-HMW-MAA antibodies comprise a light chain variable region that comprises the amino acid sequence of SEQ ID NO: 3 and a heavy chain variable region that comprises the amino acid sequence of SEQ ID NO: 6.

In some embodiments, an anti-HMW-MAA antibody binds to the epitope of human HMW-MAA bound by the murine antibody IND-1 as produced by cell line HB8759 deposited with the ATCC. In other embodiments, an anti-HMW-MAA antibody binds to the epitope of human HMW-MAA bound by the murine antibody IND-2 as produced by the cell line HB8760.

In some embodiments, an anti-HMW-MAA binding antibody or binding fragment thereof competes with the binding of an antibody comprising a light chain variable region comprising the amino acid sequence of SEQ ID NO: 7 and a heavy chain variable region comprising the amino acid sequence of SEQ ID NO: 10 to human HMW-MAA.

In some embodiments, an anti-HMW-MAA antibody or binding fragment thereof competes with the binding of an antibody comprising a light chain variable region comprising the amino acid sequence of SEQ ID NO: 1 and a heavy chain variable region comprising the amino acid sequence of SEQ ID NO: 4 to human HMW-MAA.

In some embodiments, an anti-HMW-MAA antibody binds HMW-MAA with high affinity (e.g., about 10 to 0.1 nM or stronger). In some embodiments, an anti-HMW-MAA antibody has low immunogenicity.

In some embodiments, an anti-HMW-MAA antibody is active in assays of antibody dependent cellular cytotoxicity (ADCC) and/or in assays of complement mediated cytotoxicity (CDC).

In some embodiments, an anti-HMW-MAA antibody is a full length antibody. In some embodiments, an anti-HMW-MAA antibody is a human IgG.

In some embodiments, an anti-HMW-MAA antibody is an antibody fragment (e.g., binding fragment). In some embodiments, the anti-HMW-MAA antibody is a Fab, Fab', Fab'-SH, Fv, scFv, F(ab')$_2$or SCA (single chain antibody).

In some embodiments, an anti-HMW-MAA antibody is bound to a detectable label.

The present disclosure also provides immobilized antibodies comprising the anti-HMW-MAA antibodies as described herein bound to a solid phase.

The present disclosure also provides conjugates comprising the anti-HMW-MAA antibodies as described herein bound to a cytotoxic or non-cytotoxic agent.

The present disclosure further provides isolated nucleic acids encoding anti-HMW-MAA antibodies as described herein; a vector comprising one or more nucleic acids, optionally operably linked to control sequences recognized by a host cell transformed with the vector; a host cell comprising the nucleic acids encoding anti-HMW-MAA antibodies (e.g., a host cell transformed or transfected with one or more nucleic acids); a process for producing the antibodies comprising culturing the host cell so that the one or more nucleic acids are expressed and, optionally, recovering the antibodies from the host cell culture (e.g., from the host cell culture medium).

The present disclosure also provides pharmaceutical compositions comprising one or more anti-HMW-MAA antibodies and one or more pharmaceutically acceptable carriers or diluents.

The present disclosure also provides methods for determining the presence of a HMW-MAA protein comprising exposing a sample suspected of containing the HMW-MAA protein to anti-HMW-MAA antibodies and determining binding of the antibodies to the sample.

The present disclosure also provides for diagnostic and therapeutic uses of anti-HMW-MAA antibodies.

The present disclosure also provides a method of killing or inhibiting the growth of an HMW-MAA expressing cancer cell comprising contacting the cell with an amount of a anti-HMW-MAA antibody effective to kill or inhibit the cell.

The present disclosure also provides a method of inhibiting metastasis of HMW-MAA expressing cancer cells comprising administering an amount of the anti-HMW-MAA antibodies as described herein effective to inhibit the metastasis of the cells. For such methods, other agents such as a cytotoxic, non-cytotoxic, or chemotherapeutic agent, may be used to contact the cells, for example, by administration either before, after, or simultaneously with, or by conjugation to, the anti-HMW-MAA antibody.

The present disclosure also provides methods for treating a mammal suffering from a disease or disorder associated with expression of HMW-MAA comprise administering a pharmaceutically effective amount of anti-HMW-MAA antibodies to the mammal. The methods may further comprise administering a chemotherapeutic agent before, after or simultaneously with the anti-HMW-MAA antibodies. In some embodiments, the disease or disorder is cancer including, for example, melanoma, basal cell carcinoma, acute lymphoblastic leukemia (ALL) or acute myeloid leukemia/acute myelogenous leukemia (AML).

The present disclosure also provides a kit comprising anti-HMW-MAA antibodies as described herein and instructions for using the anti-HMW-MAA antibodies to detect the HWM-MAA protein.

BRIEF DESCRIPTION OF THE DRAWINGS

The foregoing summary, as well as the following detailed description of the disclosure, will be better understood when read in conjunction with the appended figures. For the purpose of illustrating the disclosure, shown in the figures are embodiments which are presently preferred. It should be understood, however, that the disclosure is not limited to the precise arrangements, examples and instrumentalities shown.

DETAILED DESCRIPTION

Figure 1:
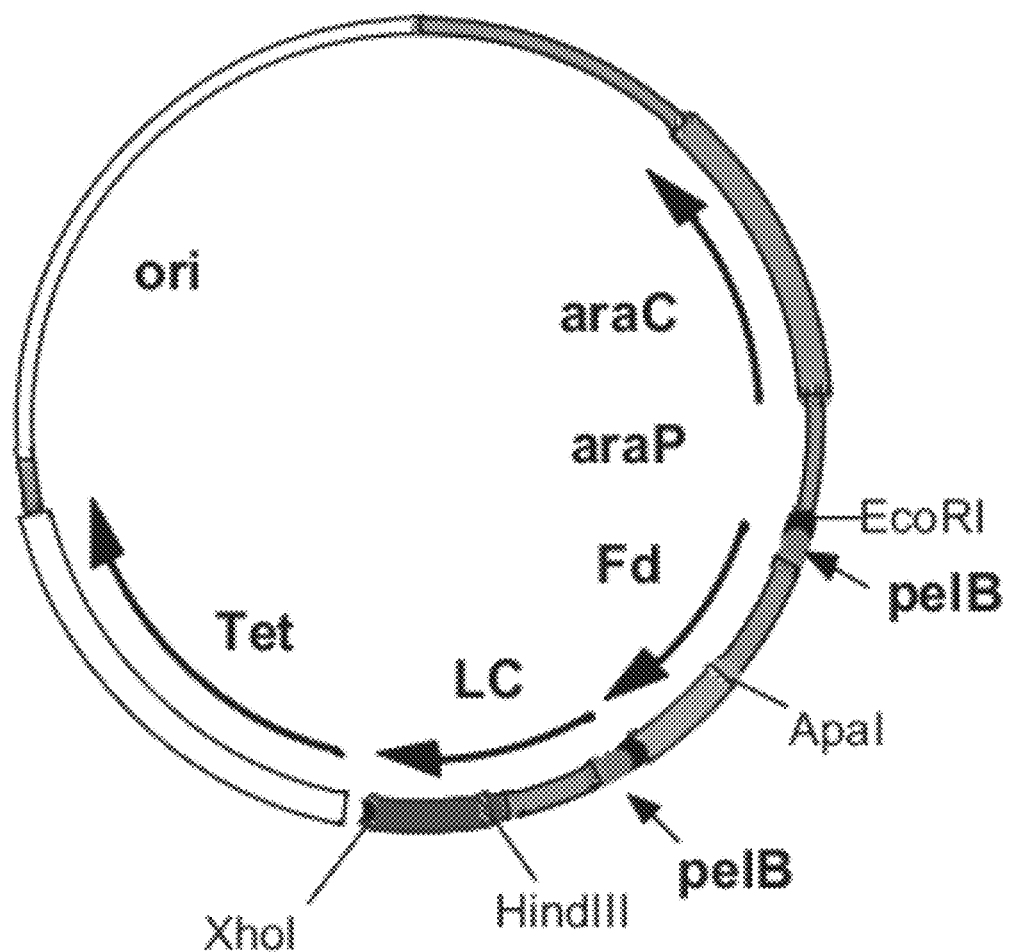
FIG. 1 shows a Fab expression vector.

The present disclosure provides anti-HMW-MAA antibodies or binding fragments thereof (e.g., Fabs) which bind with high affinity to human HMW-MAA. The anti-HMW-MAA antibodies may comprise a light chain variable region comprising the amino acid sequence of SEQ ID NO: 2 or SEQ ID NO: 3 and a heavy chain variable region comprising the amino acid sequence of SEQ ID NO: 5 or SEQ ID NO 6. Alternatively, the anti-HMW-MAA antibodies may comprise a light chain variable region comprising the amino acid sequence of SEQ ID NO: 8 or SEQ ID NO: 9 and a heavy chain variable region comprising the amino acid sequence of SEQ ID NO: 11 or SEQ ID NO 12.

Anti-HMW-MAA antibodies as described herein include those comprising novel variable regions with sequences derived from murine monoclonal antibodies such as IND-1 and IND-2. IND-1 and IND-2 are murine monoclonal antibodies that recognize non-overlapping epitopes of HMW-MAA (see, e.g., hybridoma XMMME-001 and XMMME-002 deposited with the American Type Culture Collection (ATCC) on Mar. 26, 1985 and given Accession Nos. HB8759 and H88760, respectively). Human engineered anti-HMW-MAA antibodies were created by changing one or more of the plethora of amino acid residues in the variable regions of heavy and light chains of antibodies identified in Studnicka et al. (U.S. Pat. No. 5,766,886; "the '886 patent") as being candidates for change. The '886 patent identified seventy-three low risk positions in antibody light and heavy chain variable regions (thirty-eight in the light chain variable region and thirty-five in the heavy chain variable region) and twenty-nine moderate risk positions in antibody light and heavy chain variable regions (twelve in the light chain variable region and seventeen in the heavy chain variable region) as being candidates for change. For example, the '886 patent shows low risk positions in the variable regions as circles and moderate risk positions in the variable regions as triangles in the lines labeled "risk" in FIGS. 1A, 1B, 5A, 5B, 6A, 6B, 10A and 10B. The human engineered anti-HMW-MAA antibodies comprise a selected subset of low and/or moderate risk amino acid residues and unexpectedly bind to HMW-MAA with high affinity. Such antibodies may exhibit reduced immunogenicity as compared to a murine antibody. These antibodies may be used to treat diseases or disorders characterized by expression of HMW-MAA including, for example, cancer (e.g., melanoma, basal cell carcinoma, ALL or AML).

The present disclosure provides anti-high molecular weight melanoma associated antigen (HMW-MAA) antibodies (e.g., Fabs) which bind to human HMW-MAA comprising a light chain variable region comprising the amino acid sequence of SEQ ID NO: 2 and a heavy chain variable region comprising the amino acid sequence of SEQ ID NO: 5. In some embodiments, the anti-HMW-MAA antibody or binding fragment thereof competes with the binding of an antibody comprising a light chain variable region comprising the amino acid sequence of SEQ ID NO: 1 and a heavy chain variable region comprising the amino acid sequence of SEQ ID NO: 4 to human HMW-MAA.

The present disclosure provides anti-high molecular weight melanoma associated antigen (HMW-MAA) antibodies (e.g., Fabs) which bind to human HMW-MAA comprising a light chain variable region comprising the amino acid sequence of SEQ ID NO: 3 and a heavy chain variable region comprising the amino acid sequence of SEQ ID NO 6. In some embodiments, the anti-HMW-MAA antibody or binding fragment thereof competes with the binding of an antibody comprising a light chain variable region comprising the amino acid sequence of SEQ ID NO: 1 and a heavy chain variable region comprising the amino acid sequence of SEQ ID NO: 4 to human HMW-MAA.

The present disclosure also provides anti-high molecular weight melanoma associated antigen (HMW-MAA) antibodies (e.g., Fabs) which bind to human HMW-MAA comprising a light chain variable region comprising the amino acid sequence of SEQ ID NO: 8 and a heavy chain variable region comprising the amino acid sequence of SEQ ID NO: 11. In some embodiments, the anti-HMW-MAA binding antibody or binding fragment thereof competes with the binding of an antibody comprising a light chain variable region comprising the amino acid sequence of SEQ ID NO: 7 and a heavy chain variable region comprising the amino acid sequence of SEQ ID NO: 10 to human HMW-MAA.

The present disclosure also provides anti-high molecular weight melanoma associated antigen (HMW-MAA) antibodies (e.g., Fabs) which bind to human HMW-MAA comprising a light chain variable region comprising the amino acid sequence of SEQ ID NO: 9 and a heavy chain variable region comprising the amino acid sequence of SEQ ID NO 12. In some embodiments, the anti-HMW-MAA binding antibody or binding fragment thereof competes with the binding of an antibody comprising a light chain variable region comprising the amino acid sequence of SEQ ID NO: 7 and a heavy chain variable region comprising the amino acid sequence of SEQ ID NO: 10 to human HMW-MAA.

The antibodies as described herein may be used for treating a mammal suffering from a disease or disorder associated with expression of HMW-MAA, comprising administering an effective such as a therapeutically effective amount of the anti-HMW-MAA antibodies as disclosed herein to the mammal. Such methods may further comprising administering a chemotherapeutic agent before, after or simultaneously with the anti-HMW-MAA antibody. In some embodiments, the disease or disorder is cancer including, for example, melanoma, basal cell carcinoma, AML or ALL.

A. Antibody Preparation

A method for human engineering a non-human HMW-MAA antibody is described in the Examples below. In order to human engineer an anti-HMW-MAA antibody, the non-human antibody starting material is prepared. Exemplary techniques for generating such antibodies will be described in the following sections.

(1) Antigen Preparation

The HMW-MAA antigen to be used for production of antibodies may be a soluble form of the HMW-MAA antigen or other fragment of HMW-MAA (e.g. an HMW-MAA fragment comprising the epitope recognized by IND-1 or IND-2). Alternatively, cells expressing HMW-MAA at their cell surface can be used to generate antibodies. Such cells can be transformed to express HMW-MAA or may be other naturally occurring cells. Other forms of HMW-MAA useful for generating antibodies will be apparent to those skilled in the art.

(2) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

(3) Monoclonal Antibodies

Monoclonal antibodies may be made using the hybridoma method first described by Kohler et al., Nature, 256: 495 (1975), or may be made by recombinant DNA methods (U.S. Pat. No. 4,816,567). The term monoclonal antibody refers to an antibody obtained from a population of substantially homogeneous antibodies, e.g., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier monoclonal indicates the character of the antibody as being obtained from a substantially homogeneous population of antibodies, and is not to be construed as requiring production of the antibody by any particular method. For example, the monoclonal antibodies may be made by the hybridoma method first described by Kohler et al., Nature 256: 495 (1975), or may be made by recombinant DNA methods (See, e.g., U.S. Pat. No. 4,816,567). The monoclonal antibodies may also be isolated from phage antibody libraries, for example, using the techniques described in Clackson et al., *Nature* 352: 624-628 (1991) and Marks et al., *J. Mol. Biol.* 222: 581-597 (1991).

The monoclonal antibodies herein specifically include chimeric antibodies (immunoglobulins) in which a portion of the heavy and/or light chain is identical with or homologous to corresponding sequences in antibodies derived from one antibody sequence, including those derived from a particular species or belonging to a particular antibody class or subclass, while the remainder of the chain(s) is identical with or homologous to corresponding sequences in antibodies derived from another antibody sequence, including those derived from another species or belonging to another antibody class or subclass, as well as fragments of such antibodies, on long as they exhibit the desired biological activity [see, e.g., U.S. Pat. No. 4,816,567; and Morrison et al., *Proc. Natl. Acad Sci. USA* 81: 6851-6855 (1984)].

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson at al., Anal. Biochem., 107: 220 (1980). After hybridoma cells are identified that produce antibodies of the desired specificity, affinity, and/or activity, the clones may be subcloned by limiting dilution procedures and grown by standard methods (Goding, Monoclonal Antibodies; Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies will be described in more detail below.

(4) Human Engineering and Amino Acid Sequence Variants

Example 1 below describes methods for the human engineering of anti-HMW-MAA antibodies. In certain embodiments, it may be desirable to generate amino acid sequence variants of the human engineered antibody, particularly where these improve the binding affinity or other biological properties of the human engineered antibody.

Amino acid sequence variants of human engineering anti-HMW-MAA antibody are prepared by introducing appropriate nucleotide changes into a human engineered anti-HMW-MAA antibody DNA, or by peptide synthesis. Such variants include, for example, deletions from, and/or insertions into and/or substitutions of, residues within the amino acid sequences shown for the human engineered anti-HMW-MAA antibodies. Any combination of deletion, insertion, and substitution is made to arrive at the final construct, provided that the final construct possesses the desired characteristics. The amino acid changes also may alter post-translational processes of the humanized anti-HMW-MAA antibody, such as changing the number or position of glycosylation sites.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include human engineered anti-HMW-MAA antibody with an N-terminal methionyl residue or the antibody fused to an epitope tag. Other insertional variants of the human engineered anti-HMW-MAA antibody molecule include the fusion to the N- or C-terminus of human engineered anti-HMW-MAA antibody of an enzyme or a polypeptide which increases the serum half-life of the antibody.

Another type of variant is an amino acid substitution variant. These variants have at least one amino acid residue in the human engineered anti-HMW-MAA antibody molecule removed and a different residue inserted in its place. The sites of greatest interest for substitutional mutagenesis include the hypervariable loops, but framework (FR) alterations are also contemplated. Hypervariable region residues or FR residues involved in antigen binding are generally substituted in a relatively conservative manner. Such conservative substitutions are shown below under the heading of preferred substitutions. If such substitutions result in a change in biological activity, then more substantial changes, denominated exemplary substitutions as shown below or as further described below in reference to amino acid classes, are introduced and the products screened.

The term hypervariable region refers to the amino acid residues of an antibody which are responsible for antigen-binding. The hypervariable region comprises amino acid residues from a complementarity determining region or CDR [e.g., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (e.g., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., *J. Mol. Biol.* 196:

901-917 (1987)]. Framework or FR residues are those variable domain residues other than the hypervariable region residues.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: met, ala, val, leu, ile; (2) neutral hydrophilic: cys, ser, thr; (3) acidic: asp, glu; (4) basic: asn, gln, his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the human engineered anti-HMW-MAA antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of a human engineered anti-HMW-MAA antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of human engineered anti-HMW-MAA antibody. Ordinarily, amino acid sequence variants of the human engineered anti-HMW-MAA antibody will have an amino acid sequence having at least 75% amino acid sequence identity with the original human engineered antibody amino acid sequences of either the heavy or the light chain (e.g., as in SEQ ID NO: 2, 3, 5, 6, 8, 9, 11 or 12) more preferably at least 80%, more preferably at least 85%, more preferably at least 90%, and most preferably at least 95%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%. Identity or homology with respect to this sequence is defined herein as the percentage of amino acid residues in the candidate sequence that are identical with the human engineered anti-HMW-MAA residues, after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the antibody sequence shall be construed as affecting sequence identity or homology. Thus, sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a predetermined portion of one or both sequences). The programs provide a default opening penalty and a default gap penalty, and a scoring matrix such as PAM 250 [a standard scoring matrix; see Dayhoff et al., in *Atlas of Protein Sequence and Structure*, vol. 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

(5) Screening for Biological Properties

Antibodies are screened for the characteristics identified herein as being desirable in a human engineered anti-HMW-MAA antibody.

To screen for antibodies which bind to the epitope on HMW-MAA bound by an antibody of interest (e.g., those which compete for the binding of anti-HMW-MAA antibodies as described herein, for example, antibodies that comprise a light chain variable region comprising the amino acid sequence of SEQ ID NO: 8 or SEQ ID NO: 9 and a heavy chain variable region comprising the amino acid sequence of SEQ ID NO: 11 or SEQ ID NO 12, or alternatively, a light chain variable region comprising the amino acid sequence of SEQ ID NO: 2 or SEQ ID NO: 3 and a heavy chain variable region comprising the amino acid sequence of SEQ ID NO: 5 or SEQ ID NO 6), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al., J. Biol. Chem. 270: 1388-1394 (1995), can be performed to determine whether the antibody binds an epitope of interest.

Antibody affinities (e.g. for human HMW-MAA may be determined by saturation binding using cells expressing HMW-MAA. Preferred human engineered antibodies are those which bind human HMW-MAA with a $K_d$ value of no more than about $1\times10^{-7}$M; preferably no more than about $1\times10^{-8}$M; more preferably no more than about $1\times10^{-9}$M; and most preferably no more than about $1\times10^{-10}$M. R is also desirable to select human engineered antibodies which have beneficial ADCC and/or CDC properties as described in Example 4 below.

(6) Antibody Fragments

In certain embodiments, a human engineered HMW-MAA antibody may be an antibody fragment (e.g., a $F(ab)_2$, Fab, Fv or ScFv). Antibody fragments are portions of an intact full length antibody, such as an antigen binding or variable region of the intact antibody. Examples of antibody fragments include Fab, Fab', $F(ab')_2$, and Fv fragments; dsFvs, dAbs, diabodies; linear antibodies; single-chain antibody molecules (e.g., scFv); unibodies, one-armed antibodies, multispecific antibody fragments such as bispecific, trispecific, and multispecific antibodies (e.g., bispecific T-cell engagers (BiTE's), diabodies, triabodies, tetrabodies); minibodies; chelating recombinant antibodies; tribodies or bibodies; intrabodies; nanobodies; small modular immunopharmaceuticals (SMTP), binding-domain immunoglobulin fusion proteins; camelized antibodies: $V_{HH}$ containing antibodies; and any other polypeptides formed from antibody fragments.

Various techniques have been developed for the production of antibody fragments. Traditionally, these fragments were derived via proteolytic digestion of intact antibodies (See, e.g., Morimoto et al., Journal of Biochemical and Biophysical Methods 24: 107-117 (1992) and Brennan et al., Science 229: 81 (1985)). However, these fragments can now be produced directly by recombinant host cells (Holliger and Hudson Nat. Biotech. 23: 1126-1136 (2005)). A multiplicity of antibody fragments can be made in bacteria, for example, Fab'-SH fragments can be recovered from E. coli and chemically coupled to form F(ab')$_2$ fragments (Carter at al., Bio/Technology 10:163-167 (1992)). According to another approach, F(ab')$_2$ fragments can be isolated directly from recombinant host cell culture. Other techniques for the production of antibody fragments will be apparent to the skilled practitioner.

(7) Multispecific Antibodies

In some embodiments, it may be desirable to generate multispecific (e.g. bispecific) human engineered HMW-MAA antibodies having binding specificities for at least two different epitopes. Exemplary bispecific antibodies may bind to two different epitopes of the HMW-MAA protein. Alternatively, an anti-HMW-MAA arm may be combined with an arm which binds to a triggering molecule on a leukocyte such as a T-cell receptor molecule (e.g., CD2 or CD3), or Fc receptors for IgG (FcγR), such as FcγRI (CD64), FcγRII (CD32) and FcγRIII (CD16) so as to focus cellular defense mechanisms to the HMW-MAA-expressing cell. Bispecific antibodies may also be used to localize cytotoxic agents to cells which express HMW-MAA. These antibodies possess an HMW-MAA-binding arm and an arm which binds the cytotoxic agent (e.g., saporin, anti-interferon-alpha, vinca alkaloid, ricin A chain, methotrexate or radioactive isotope hapten). Bispecific antibodies can be prepared as full length antibodies or antibody fragments (e.g., F(ab')$_2$bispecific antibodies).

According to another approach for making bispecific antibodies, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory cavities of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers (see, e.g., WO96/27011).

Bispecific antibodies include cross-linked or heteroconjugate antibodies. For example, one of the antibodies in the heteroconjugate can be coupled to avidin, the other to biotin. Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Fab'-SH fragments recovered from E. coli, can be chemically coupled to form bispecific antibodies. Shalaby et al., J. Exp. Med. 175:217-225 (1992) describe the production of a fully humanized bispecific antibody F(ab')$_2$ molecule. Each Fab' fragment was separately secreted from E. coli and subjected to directed chemical coupling in vitro to form the bispecific antibody. The bispecific antibody thus formed was able to bind to cells overexpressing the HER2 receptor and normal human T cells, as well as trigger the lytic activity of human cytotoxic, lymphocytes against human breast tumor targets.

Various techniques for making and isolating bispecific antibody fragments directly from recombinant cell culture have also been described. For example, bispecific antibodies have been produced using leucine zippers [Kostelny at al., J. Immunol. 148(5): 1547-1553 (1992)]. The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The diabody technology described by Hollinger at al., Proc. Natl. Acad. Sci. USA 90: 6444-6448 (1993) has provided an alternative mechanism for making bispecific antibody fragments. The fragments comprise a heavy chain variable region ($V_H$) connected to a light-chain variable region ($V_L$) by a linker which is too short to avow pairing between the two domains on the same chain. Accordingly, the $V_H$ and $V_L$ domains of one fragment are forced to pair with the complementary $V_L$ and $V_4$ domains of another fragment, thereby forming two antigen-binding sites. Another strategy for making bispecific antibody fragments by the use of single-chain Fv (sFv) dimers has also been reported. See Gruber et al., J. Immunol. 152: 5368 (1994). Alternatively, the bispecific antibody may be a linear antibody produced as described in Zapata at al. Protein Eng. 8(10): 1057-1062 (1995).

(8) Other Modifications

Other modifications of a human engineered anti-HMW-MAA antibody are contemplated. For example, it may be desirable to modify the antibody as described herein with respect to effector function, so as to enhance the effectiveness of the antibody in treating cancer, for example (Natsume et al, Drug Design, Dev't and Ther. 3: 7-16 (2009).

ADCC refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing.

The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (USA) 95:652-656 (1998).

It may be desirable to modify an antibody as described herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule. Other techniques for modulating serum half-life include PEGylation, and fusion to serum albumin (Carter, Nat. Reviews Immunol. 6: 343-357 (2006).

(a) Immunoconjugates

The present disclosure also pertains to immunoconjugates comprising an antibody as described herein conjugated to a cytotoxic agent such as a chemotherapeutic agent (e.g., doxorubicin), a growth inhibitory agent, a toxin (e.g., an enzymatically active toxin of bacterial, fungal, plant, or animal origin, or fragments thereof), or a radioactive isotope (e.g., a radioconjugate). An additional agent may be conjugated (e.g., linked directly or indirectly by chemical or recombinant/ genetic means) to an antibody.

A cytotoxic agent refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic. A non-cytotoxic agent may include a bead, liposome, matrix or particle (see, e.g., U.S. Patent Publications 200310028071 and 2003/ 0032995 which are incorporated by reference herein). Such agents may be conjugated, coupled, linked or associated with a human engineered anti-HMW-MAA antibody as described herein.

A chemotherapeutic agent is a chemical compound useful in the treatment of cancer. Examples of chemotherapeutic agents include Adriamycin, Doxorubicin, 5-Fluorouracil, Folinic acid, Cytosine arabinoside (Ara-C), Cyclophosphamide, Thiotepa, Taxotere (docetaxel), Busulfan, Cytoxin, Taxol, Methotrexate, Cisplatin, Dolastatin, Auristatin, CPT-11, (Irinotecan, CAMPTOSAR), Gemcitabine (Gemzar®) Melphalan, Vinblastine, Bleomycin, Etoposide, Ifosfamide, Mitomycin C, Mitoxantrone, Vincreistine, Vinorelbine, Carboplatin, Teniposide, Daunomycin, Carminomycin, Aminopterin Dactinomycin, Mitomycins, Esperamicins (see, e.g., U.S. Pat. No. 4,675,187), Melphalan and other related nitrogen mustards. Label refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

In certain embodiments, an immunoconjugate comprises an antibody and a chemotherapeutic agent or other toxin. Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{131}In$, $^{90}Y$, and $^{18}Re$. Conjugates of the antibody and cytotoxic agent may be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta at al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94111026.

Conjugates of an antibody and one or more small molecule toxins, such as a calicheamicin, auristatin peptides, such as monomethylauristatin (MMAE) (synthetic analog of dolastatin), maytansinoids, such as DM1, a trichothene, and CC1065, and the derivatives of these toxins that have toxin activity, are also contemplated herein.

The use of antibody-drug conjugates for the local delivery of cytotoxic or cytostatic agents, e.g. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1966):603-05; Thorpe, (1985) "Antibody Carriers Of Cytotoxic Agents In Cancer Therapy: A Review," in Monoclonal Antibodies '84: Biological And Clinical Applications, A. Pinchera at al. (ed.s), pp. 475-506). Maximal efficacy with minimal toxicity is sought thereby. Both polyclonal antibodies and monoclonal antibodies have been reported as useful in these strategies (Rowland at al., (1986) Cancer Immunol. Immunother., 21:183-87). Drugs used in these methods include daunomycin, doxorubicin, methotrexate, and vindesine (Rowland at al., (1986) supra). Toxins used in antibody-toxin conjugates include bacterial toxins such as diphtheria toxin, plant toxins such as ricin, small molecule toxins such as geldanamycin (Mandler et al (2000) Jour of the Nat. Cancer Inst. 92(19): 1573-1581; Mandler at al (2000) Bioorganic & amp; Med. Chem. Letters 10:1025-1028; Mandler et al (2002) Bioconjugate Chem. 13.786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect theft cytotoxic and cytostatic effects by mechanisms including tubulin binding, DNA binding, or topoisomerase inhibition.

Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and 111 In or 90Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG; (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7); 686; U.S. Pat. Nos. 4,970,198; 5,079,233; 5,585,089; 5,606,040; 5,693,762; 5,739,116; 5,767,285; 5,773,001). The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cACIO (specific to CD30 on hematological malignancies) (Doronina et al (2003) Nature Biotechnology 21(7):778-784) for therapeutic development. Further examples of immunotoxins in development are described in Pastan et al Nat. Reviews, Cancer 6: 559-565 (2006).

Chemotherapeutic agents useful in the generation of immunoconjugates are described herein. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include 212Bi, 131 1, 131 In, 90Y, and 186Re.

In some embodiments, the immunoconjugate comprises an anti-HMW-MAA antibody (full length or fragments) as described herein conjugated to one or more maytansinoid molecules. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151, 042). Synthetic maytansinol and derivatives and analogues thereof are disclosed, for example, in U.S. Pat. Nos. 4,137, 230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible, to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Maytansine compounds suitable for use as maytansinoid drug moieties are well known in the art, and can be isolated from natural sources according to known methods, produced using genetic engineering techniques (see Vu et al (2002) PNAS 99:7968-7973), or maytansinol and maytansinol analogues prepared synthetically according to known methods.

Exemplary maytansinoid drug moieties include those having a modified aromatic ring, such as: C-19-dechloro (U.S. Pat. No. 4,256,746) (prepared by lithium aluminum hydride reduction of ansamytocin P2); C-20-hydroxy (or C-20-demethyl)+/−C-19-dechloro (U.S. Pat. Nos. 4,361,650 and 4,307, 016) (prepared by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared by acylation using acyl chlorides) and those having modifications at other positions Exemplary maytansinoid drug moieties also include those having modifications such as: C-9-SH (U.S. Pat. No. 4,424, 219) (prepared by the reaction of maytansinol with H2S Or P2S5); C-14-alkoxymethyl(demethoxy/CH 2 OR) (U.S. Pat. No. 4,331,598); C-14-hydroxymethyl or acyloxymethyl (CH2OH or CH2OAc) (U.S. Pat. No. 4,450,254) (prepared from Nocardia); C-15-hydroxy/acyloxy (U.S. Pat. No. 4,364, 866) (prepared by the conversion of maytansinol by *Streptomyces*); C-15-methoxy (U.S. Pat. Nos. 4,313,946 and 4,315, 929) (isolated from *Trewia nudiflora*); C-18-N-demethyl (U.S. Pat. Nos. 4,362,663 and 4,322,348) (prepared by the demethylation of maytansinol by *Streptomyces*); and 4,5-deoxy (U.S. Pat. No. 4,371,533) (prepared by the titanium trichloride/LAH reduction of maytansinol).

Exemplary embodiments of maytansinoid drug moieities include: DMI; DM3; and DM4, HERCEPTIN® (trastuzumab) linked by SMCC to DMI has been reported (WO 2005/037992, which is expressly incorporated herein by reference in its entirety). An antibody drug conjugate as described herein may be prepared according to the procedures disclosed therein.

Immunoconjugates containing maytansinoids, methods of making same, and theft therapeutic use are disclosed, for example, in U.S. Pat. Nos. 5,208,020; 5,416,064; 6,441,163 and European Patent EP 0 425 235 B1. Liu at al., Proc. Natl. Acad. Sci. USA 93:8618-8623 (1996) described immunoconjugates comprising a maytansinoid designated DMI linked to the monoclonal antibody C242 directed against human colorectal cancer. The conjugate was found to be highly cytotoxic towards cultured colon cancer cells, and showed antitumor activity in an in vivo tumor growth assay. Chad at al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Anti-STEAP-1 antibody-maytansinoid conjugates are prepared by chemically linking an antibody to a maytansinoid molecule without significantly diminishing the biological activity of either the antibody or the maytansinoid molecule (see, e.g., U.S. Pat. No. 5,208,020). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and non-patent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020, 6,441,163, or EP Patent 0 425 235 B1, Chad et al., Cancer Research 52:127-131 (1992), and US 2005/0169933 A1. Antibody-maytansinoid conjugates comprising the linker component SMCC may be prepared as disclosed in U.S. patent application Ser. No. 11/141,344, filed 31 May 2005, "Antibody Drug Conjugates and Methods". The linking groups include disulfide groups, thioether groups, acid labile groups, photolabile groups, peptidase labile groups, or esterase labile groups, as disclosed in the above-identified patents. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-l-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

Particularly preferred coupling agents include N-succinimidyl-3-(2-pyridyldithio) propionate (SPDP) (Carlsson et al, Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

In one embodiment, any of the antibodies as described herein (full length or fragment) are conjugated to one or more maytansinoid molecules. In one embodiment of the immunoconjugate, the cytotoxic agent D, is a maytansinoid DM1. In one embodiment of the immunoconjugate, the linker is selected from the group consisting of SPDP, SMCC, IT, SPDP, and SPP.

In some embodiments, the immunoconjugate comprises an antibody as described herein conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663, 149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Senter et al, Proc. AACR, 45, Abstract Number 623, presented Mar. 28, 2004. An exemplary auristatin embodiment is MMAE. Another exemplary auristatin embodiment is MMAF (US 200510238649).

Additional exemplary embodiments comprising MMAE or MMAF and various linker components have the following abbreviations (wherein Ab means antibody): Ab-MC-vc-PAB-MMAF Ab-MC-vc-PAB-MMAE Ab-MC-MMAE Ab-MC-MMAF.

Typically, peptide-based drug moieties can be prepared by forming a peptide bond between two or more amino acids and/or peptide fragments. Such peptide bonds can be prepared, for example, according to the liquid phase synthesis method.

In other embodiments, the immunoconjugate comprises an antibody as described herein conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712, 374, 5,714,586, 5,739,116, 5,767,285, 5,770,701, 5,770,710, 5,773,001, 5,877,296 (all to American Cyanamid Company). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances theft cytotoxic effects.

Other antitumor agents that can be conjugated to the antibodies as described herein include, for example, BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from Pseudomonas aeruginosa), ricin A chain, abrin A chain, modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present disclosure further contemplates an immunoconjugate formed between an antibody and a compound with nucleolytic activity (e.g., a ribonuclease or a DNA endonuclease such as a deoxyribonuclease; DNase). For selective destruction of the tumor, the antibody may comprise a highly radioactive atom. A variety of radioactive isotopes are available for the production of radioconjugated antibodies. Examples include At211, I131, I125, Y90, Re186, Re188, Sm153, Bi212, P32, Pb212 and radioactive isotopes of Lu. When the conjugate is used for detection, it may comprise a radioactive atom for scintigraphic studies, for example Tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron. The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as Tc99m or I123, Re186, Re188 and In111 can be attached via a cysteine residue in the peptide. Yttrium-90 can be attached via a lysine residue. The IODOGEN method (Fraker at al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled I-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the disclosure expressly contemplate, but are not limited to, antibody drug conjugates prepared with cross-linker reagents: BMPS, EMCS, GMBS, HBVS, LC SMCC, MBS, MPBH, SBAP, SIA, BIAS, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Anti-HMW-MAA antibodies as described herein may be conjugated to one or more drug moieties (D), e.g. about 1 to about 20 drug moieties per antibody, through a linker (L). In one embodiment, the number of drug moieties (D) per antibody is from about 1 to about 5, alternatively, from about 2 to about 6, alternatively, from about 2 to about 5, alternatively from about 3 to about 4 drug moieties per antibody. Because the number of drug moieties per antibody is typically an average number over all conjugates in a population of an antibody drug conjugate, the number of drug moieties per antibody may not be a whole number. Antibody drug conjugates may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl) cyclohexane-1 carboxylate ("SMCC"), and N-Succinimidyl (4-iodo-acetyl) aminobenzoate ("STAB"). In one embodiment, the linker is valine-citrullin-p-aminobenzyloxycaronyl ("vc-PAB"). Additional linker components are known in the art and some are described herein.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or vat-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in theft selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, e.g. cysteine bridges, Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Trout's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates may also be produced by modification of the antibody to introduce electrophilic moieties, which can react with nucleophilic subsituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & amp; Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Methods for the conjugation of linker-drug moieties to cell-targeted proteins such as antibodies, immunoglobulins or fragments thereof are found, for example, in U.S. Pat. No. 5,208,020; U.S. Pat. No. 6,441,163; WO 2005/037992; WO 2005/08171; and WO 2006/034488. Alternatively, a fusion protein comprising the antibody and cytotoxic agent may be made, e.g., by recombinant techniques or peptide synthesis. The length of DNA may comprise respective regions encoding the two portions of the conjugate either adjacent to one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

The following embodiments are further provided. In one embodiment, an immunoconjugate has in vitro or in vivo cell killing activity. In one embodiment, the linker is attached to the antibody through a thiol group on the antibody. In one embodiment, the linker is cleavable by a protease. In one embodiment, the linker comprises a val-cit dipeptide. In one embodiment, the linker comprises a p-aminobenzyl unit. In one embodiment, the p-aminobenzyl unit is disposed between the drug and a protease cleavage site in the linker. In one embodiment, the p-aminobenzyl unit is p-aminobenzyloxycarbonyl (PAB). In one embodiment, the linker comprises 6-maleimidocaproyl. In one embodiment, the 6-maleimidocaproyl is disposed between the antibody and a protease cleavage site in the linker. The above embodiments may occur singly or in any combination with one another.

In another embodiment, antibodies may be labelled through the cysteine thiol with radionuclides, fluorescent dyes, bioluminescence-triggering substrate moieties, chemiluminescence-triggering substrate moieties, enzymes, and other detection labels for imaging experiments with diagnostic, pharmacodynamic, and therapeutic applications. Generally, the labelled cysteine engineered antibody, e.g. "biomarker" or "probe", is administered by injection, perfusion, or oral ingestion to a living organism, e.g. human, rodent, or other small animal, a perfused organ, or tissue sample. The distribution of the probe is detected over a time course and represented by an image.

The HMW-MAA antibodies disclosed herein may also be formulated as immunoliposomes. Liposomes containing the antibody are prepared by methods known in the art, such as described in Epstein at al., Proc. Natl. Acad. Sci. USA 82: 3688 (1985): Hwang at al., Proc. Natl. Acad. Sci. USA 77: 4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody as described herein can be conjugated to the liposomes as described in Martin et al., J. Biol. Chem. 257: 286-288 (1982) via a disulfide interchange reaction. A chemotherapeutic agent (such as Doxorubicin) is optionally contained within the liposome [see, e.g., Gabizon et al., National Cancer inst. 81(19): 1484 (1989)].

Human engineered antibodies a described herein may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in methods as described herein include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as abzymes, can be used to convert the prodrugs as described herein into free active drugs (See, e.g., Massey, Nature 328: 457-458 (1987)). Antibody-abzyme conjugates can be prepared as described herein for delivery of the abzyme to a tumor cell population.

The enzymes as described herein can be covalently bound to the anti-HMW-MAA antibodies by techniques well known in the art such as the use of the heterobifunctional crosslinking reagents discussed above. Alternatively, fusion proteins comprising at least the antigen binding region of an antibody as described herein linked to at least a functionally active portion of an enzyme a described herein can be constructed using recombinant DNA techniques well known in the art (See, e.g., Neuberger et al., Nature 312: 604-608 (1984)).

In certain embodiments, it may be desirable to use an antibody fragment, rather than an intact antibody, to increase tumor penetration, for example. In this case, it may be desirable to modify the antibody fragment in order to increase its serum half-life, for example, adding molecules such as PEG or serum albumin to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO 96/32478).

Covalent modifications of the human engineered HMW-MAA antibody are also included within the scope of this disclosure. They may be made by chemical synthesis or by enzymatic or chemical cleavage of the antibody, if applicable. Other types of covalent modifications of the antibody are introduced into the molecule by reacting targeted amino acid residues of the antibody with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives, Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues, respectively. These residues are deamidated under neutral or basic conditions. The deamidated form of these residues falls within the scope of this disclosure.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W.H. Freeman & Co., San Francisco, pp. 79-36 (1983)), acetylation of the N-terminal amine, and amidation of any C-terminal carboxyl group.

Another type of covalent modification involves chemically or enzymatically coupling glycosides to the antibody. These procedures are advantageous in that they do not require production of the antibody in a host cell that has glycosylation capabilities for N or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published 11 Sep. 1987, and in Aplin and Wriston, CRC Crit. Rev. Biochem., pp. 259-306 (1981).

Removal of any carbohydrate moieties present on the antibody may be accomplished chemically or enzymatically. Chemical deglycosylation requires exposure of the antibody to the compound trifluoromethanesulfonic acid, or an equivalent compound. This treatment results in the cleavage of most or all sugars except the linking sugar (N-acetylglucosamine or N-acetylgalactosamine), while leaving the antibody intact. Chemical deglycosylation is described by Hakimuddin, at al. Arch. Biochem. Biophys. 259: 52 (1987) and by Edge et al. Anal. Biochem., 118: 131 (1981). Enzymatic cleavage of carbohydrate moieties on antibodies can be achieved by the use of a variety of endo- and exo-glycosidases as described by Thotakura et al. Meth, Enzymol. 138: 350 (1987).

Another type of covalent modification of the antibody comprises linking the antibody to one of a variety of nonproteinaceous polymers, e.g., polyethylene glycol, polypropylene glycol, or polyoxyalkylenes, for example in the manner set forth in U.S. Pat. No. 4,640,836; 4,496,689; 4,301,144; 4,670,417; 4,791,192 or 4,179,337.

B. Vectors, Host Cells and Recombinant Methods

The disclosure also provides isolated nucleic acids encoding anti-HMW-MAA antibodies, vectors and host cells comprising one or more of the nucleic acids, and recombinant techniques for the production of the antibodies. Some example techniques for antibody production are reviewed by Birch and Racher, Adv. Drug Deliv. Rev. 58: 671-85 (2006).

For recombinant production of an antibody, the nucleic acid encoding it is isolated and inserted into a replicable vector for further cloning (amplification of the DNA) or for expression. Many vectors are available. The vector components generally include, but are not limited to, one or more of the following: a signal sequence, an origin of replication, one or more marker genes, an enhancer element, a promoter, and a transcription termination sequence.

(1) Signal Sequence Component

An anti-HMW-MAA antibody as described herein may be produced recombinantly not only directly, but also as a fusion polypeptide with a heterologous polypeptide, which is preferably a signal sequence or other polypeptide having a specific cleavage site at the N-terminus of the mature protein or polypeptide, The signal sequence selected preferably is one that is recognized and processed (e.g., cleaved by a signal peptidase) by the host cell. If prokaryotic host cells do not recognize and process the native anti-HMW-MAA antibody signal sequence, the signal sequence may be substituted by a signal sequence selected, for example, from the group of the pectate lyase (e.g., pelB) alkaline phosphatase, penicillinase, Ipp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available. The DNA for such precursor region is ligated in reading frame to DNA encoding the anti-HMW-MAA antibody.

(2) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2μ plasmid origin is suitable for yeast, and various viral origins are useful for cloning vectors in mammalian cells. Generally, the origin of replication component is not needed for mammalian expression vectors (the SV40 origin may typically be used only because it contains the early region promoter).

(3) Selective Marker Component

Expression and cloning vectors may contain a selective gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs methotrexate, neomycin, histidinol, puromycin, mycophenolic acid and hygromycin.

Another example of suitable selectable markers for mammalian cells are those that enable the identification of cells competent to take up the anti-HMW-MAA antibody nucleic acid, such as DHFR, thymidine kinase, metallothionein-I and -II (e.g., primate metallothionein genes), adenosine deaminase, ornithine decarboxylase, neomycin phosphotransferase, histidinol dehydrogenase or guanine phosphoribosyltransferase.

For example, cells transformed with the DHFR selection gene may be identified by culturing all of the transformants in a culture medium that contains methotrexate (Mtx), a competitive antagonist of DHFR. An appropriate host cell when wild-type DHFR is employed is the Chinese hamster ovary (OHO) cell line deficient in DHFR activity.

Alternatively, host cells (particularly wild-type hosts that contain endogenous DHFR) transformed or co-transformed with DNA sequences encoding HMW-MAA antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418 (see, e.g., U.S. Pat. No. 4,965,199).

A suitable selection gene for use in yeast is the trpl gene present in the yeast plasmid YRp7 (Stinchcomb at al., Nature, 282: 39 (1979)). The trp1 gene provides a selection marker for a mutant strain of yeast lacking the ability to grow in tryptophan, for example, ATCC No. 44076 or PEP4-1. Jones, Genetics, 85: 12 (1977). The presence of the trpl lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene. Ura3-deficient yeast strains are complemented by plasmids bearing the ura3 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis*. Van den Berg, Bio/Technology, 8: 135 (1990). Stable multi-copy expression vectors for secretion of mature recombinant human serum albumin by industrial strains of *Kluyveromyces* have also been disclosed. Fleer et al, Bio/Technology, 9: 968-975 (1991).

(4) Promoter Component

Expression and cloning vectors usually contain a promoter that is recognized by the host organism and is operably linked to the anti-HMW-MAA antibody nucleic acid. Promoters suitable for use with prokaryotic hosts include the arabinose (e.g., araB) promoter phoA promoter, β-lactamase and lactose promoter systems, alkaline phosphatase, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding the anti-HMW-MAA antibody.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-HMW-MAA antibody transcription from vectors in mammalian host cells may be controlled, for example, by promoters obtained from the genomes of viruses such as polyoma virus, fowlpox virus, adenovirus (such as Adenovirus 2), bovine papilloma virus, avian sarcoma virus, most preferably cytomegalovirus, a retrovirus (e.g., Abelson murine leukemia virus), hepatitis-8 virus, Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297: 598-601 (1982) on expression of human α-interferon cDNA in mouse cells under the control of a thymidine kinase promoter from herpes simplex virus. Alternatively, the rows sarcoma virus long terminal repeat can be used as the promoter.

(5) Enhancer Element Component

Transcription of a DNA encoding the anti-HMW-MAA antibody as described herein by higher eukaryotes may be increased by inserting an enhancer sequence into the vector. Many enhancer sequences are now known from mammalian genes (e.g., globin, elastase, albumin, alpha-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers (see, e.g., Yaniv, Nature 297: 17-18 (1982) on enhancing elements for activation of eukaryotic promoters). The enhancer may be spliced into the vector at a position 5' or 3' to the anti-HMW-MAA antibody-encoding sequence, but is preferably located at a site 5' from the promoter.

(6) Transcription Termination Component

Expression vectors used in eukaryotic host cells (e.g., yeast, fingi, insect, plant, animal, human, or nucleated cells from other multicellular organisms) may contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding HMW-MAA antibody. One useful transcription termination component is the bovine growth hormone polyadenylation region. See WO94/11026 and the expression vector disclosed therein. Another is the mouse immunoglobulin light chain transcription terminator.

(7) Selection and Transformation of Host Cells

Suitable host cells for cloning or expressing DNA in the vectors as described herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coil*, *Enterobacter*; *Erwinia*, *Klebsiella*, *Proteus*, *Salmonella*, e.g., *Salmonella typhimurium*, *Serratia*, e.g., *Serratia marcescens*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa* or *P. fluorescens*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for HMW-MAA antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus*; *yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Suitable host cells for the expression of glycosylated anti-HMW-MAA antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been Identified. A variety of viral strains for transfection are publicly available, e.g., the L-1 variant of *Autographa californica* NPV and the Bm-5 strain of *Bombyx mori* NPV, and such viruses may be used as the virus as described herein, particularly for transfection of *Spodoptera frugiperda* cells.

Plant cell cultures of cotton, corn, potato, soybean, petunia, tomato, and tobacco can also be utilized as hosts.

Examples of useful mammalian host cell lines are Chinese hamster ovary cells, including CHOK1 cells (ATCC CCL61), DXB-11, DG-44, and Chinese hamster ovary cells/DHFR (CHO, Urlaub et al., Proc. Natl. Acad. Sci. USA 77: 4216 (1980)); monkey kidney CV1 line transformed by SV40 (COS-7, ATCC CRL 1651); human embryonic kidney line (293 or 293 cells subcloned for growth in suspension culture, [Graham et al., J. Gen Virol. 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383: 44-68 (1982)); MRC 5 cells; FS4 cells; and a human hepatoma line (Hep G2).

Host cells may be transformed or transfected with the above-described expression or cloning vectors for anti-HMW-MAA antibody production and cultured in conventional nutrient media modified as appropriate for inducing promoters, selecting transformants, or amplifying the genes encoding the desired sequences. In addition, vectors and transfected cell lines with multiple copies of transcription units separated by a selective marker are particularly useful and preferred for the expression of human engineered antibodies that target HMW-MAA.

(8) Culturing the Host Cells

The host cells used to produce the anti-HMW-MAA antibody a described herein may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58: 44 (1979), Barnes at al., Anal. Biochem. 102: 255 (1980), U.S. Pat. Nos. 4,767,704; 4,657,866; 4,927,762; 4,660,655; or 5,122,469; WO90103430; WO 87/00196; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(9) Purification of Anti-HMW-MAA Antibody

When using recombinant techniques, an antibody may be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration (see, e.g., Better at al. Science 240: 1041-1043 (1988); ICSU Short Reports 10: 105 (1990); and Proc. Natl. Acad. Sci. USA 90: 467461 (1993) describe a procedure for isolating antibodies which are secreted to the periplasmic space of *E. coli*).

An antibody composition prepared from microbial or mammalian cells can be purified using, for example, hydroxylapatite chromatography cation or avian exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark at al., *J. Immunol. Meth.* 62: 1-13 (1983)). Protein G is recommended for all mouse isotypes and for human γ3 (Guss at al., *EMBO J.* 5: 15671576 (1986)) and also for Fabs. The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

C. Pharmaceutical Compositions and Formulations

Pharmaceutical compositions and formulations of one or more anti-HMW-MAA antibodies as described herein may be prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLUTONICs™ or polyethylene glycol (PEG).

Compositions or formulations may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773.919), copolymers of L-glutamic acid and y ethyl-L-glutamate, non-degradable ethylene-vinyl acetate, degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

D. Non-Therapeutic Uses for the Antibody

Anti-HMW-MAA antibodies as described herein may be used in non-therapeutic applications including, for example, for diagnosis, prognosis, screening or purification. Anti-HMW-MAA antibodies may be useful as affinity purification reagents. In this process, the antibodies may be immobilized on a solid phase such a Sephadex resin or filter paper, using methods well known in the art. The immobilized antibody may be contacted with a sample containing the HMW-MAA protein (or fragment thereof) to be purified, and thereafter the support may be washed with a suitable solvent to remove substantially all the material in the sample except the HMW-MAA protein, which is bound to the immobilized antibody. Finally, the support may be washed with another suitable solvent, such as glycine buffer, pH 5.0, that will release the HMW-MAA protein from the antibody.

Human engineered anti-HMW-MAA antibodies may also be useful in diagnostic assays for HMW-MAA protein, e.g., detecting its expression in specific cells, tissues, or serum.

For diagnostic applications, the antibody typically will be labeled with a detectable moiety. Numerous labels are available which can be generally grouped into the following categories:

(a) Radioisotopes, such as $^{35}$S, $^{14}$C, $^{125}$I, $^{3}$H, and $^{131}$I. The antibody can be labeled with the radioisotope using the techniques described in Current Protocols in Immunology, Volumes 1 and 2, Coligen at al., Ed. Miley-Interscience, New York, N.Y., Pubs. (1991) for example, and radioactivity can be measured using scintillation counting.

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using standard techniques including, for example, those techniques disclosed in Current Protocols in Immunology, Volumes 1 and 2, supra. Fluorescence can be quantified using a fluorimeter.

(c) Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocydic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in Methods in Enzym. (ed J. Langone & H. Van Vunakis), Academic press, N.Y., 73: 147-166 (1981).

Examples of enzyme-substrate combinations include, for example: (i) Horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); (ii) alkaline phosphatase (AP) with para-Nitrophenyl phosphate as chromogenic substrate; and (iii) (β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see, e.g., U.S. Pat. Nos. 4,275,149 and 4,318,980.

Sometimes, the label is indirectly conjugated with the antibody. The skilled artisan will be aware of various techniques for achieving this. For example, the antibody can be conjugated with biotin and any of the three broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten (e.g., digoxin) and one of the different types of labels mentioned above is conjugated with an anti-hapten antibody (e.g., anti-digoxin antibody). Thus, indirect conjugation of the label with the antibody can be achieved.

In another embodiment of the invention, the anti-HMW-MAA antibody need not be labeled, and the presence thereof can be detected using a labeled antibody which binds to the HMW-MAA antibody.

The antibodies of the present invention may be employed in any known assay method, such as competitive, binding assays, direct and indirect sandwich assays, and immunoprecipitation assays. Zola, Monoclonal Antibodies: A Manual of Techniques, pp. 147-158 (CRC Press, Inc. 1987).

Competitive binding assays rely on the ability of a labeled standard to compete with the test sample analyte, for binding with a limited amount of antibody. The amount of HMW-MAA protein in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte, which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

The antibodies may also be used for in vivo diagnostic assays. Generally, the antibody may be labeled with a radionucleotide (such as $^{111}$In, $^{99}$Tc, $^{14}$C, $^{131}$I, $^{125}$I, $^{3}$H, $^{32}$P or $^{35}$S) so that the tumor can be localized using immunoscintigraphy.

E. Antibody Kits

As a matter of convenience, an anti-HMW-MAA antibody as described herein can be provided in a kit, e.g., a packaged combination of reagents, including, for example, in predetermined amounts with instructions for performing a diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

F. Therapeutic Uses for the Antibody

It is contemplated that one or more anti-HMW-MAA antibodies as described herein may be used to treat the various HMW-MAA mediated diseases, conditions and disorders, particularly to treat HMW-MAA expressing cancer cells, including, for example, a melanoma, basal cell carcinoma, ALL or AML. Treatment refers to both therapeutic treatment and prophylactic or preventative measures. Subjects including, for example, humans, in need of treatment include those already with the disorder as well as those in which disease, condition or the disorder is to be prevented. It is contemplated that an anti-HMW-MAA antibody as described herein may be used to bind to, contact, inhibit the growth of, inhibit the metastasis of and/or kill an HMW-MAA expressing cell, including an HMW-MAA expressing cancer cell, alone or in combination with another agent such as a chemotherapeutic agent. An anti-HMW-MAA antibody as described herein may be administered to a subject with an HMW-MAA mediated disease, condition or disorder, including a subject with a cancer such as melanoma, basal cell carcinoma, AML or ALL.

The anti-HMW-MAA antibody may be administered by any suitable means, including parenteral, subcutaneous, intraperitoneal, intrapulmonary, and intranasal, and, if desired for local immunosuppressive treatment, intralesional administration (including perfusing or otherwise contacting the graft with the antibody before transplantation). Parenteral infusions include intramuscular, intravenous, intraarterial, intraperitoneal, or subcutaneous administration. In addition, the anti-HMW-MAA antibody may be suitably administered by pulse infusion, particularly with declining doses of the antibody. Preferably the dosing may be given by Injections, most preferably intravenous or subcutaneous injections, depending in part on whether the administration is brief or chronic.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody may be suitably administered to the patient at one time or over a series of treatments.

Depending on the type and severity of the disease, dosage ranges include from about 0.1 ng/kg to up to about 100 mg/kg or more (in terms of active agent amount per unit of body weight of subject administered the active agent), depending on the factors mentioned above. In other embodiments, the dosage ranges from about 0.1 µg/kg to about 100 mg/kg, from about 1 µg/kg to about 100 mg/kg, from about 5 µg/kg to about 100 mg/kg, from about 0.5 mg/kg up to about 100 mg/kg, or from about 1 mg/kg up to about 100 mg/kg. For repeated administrations over several days or longer, depending on the condition, the treatment is sustained until a desired suppression of disease symptoms occurs. However, other dosage regimens may be useful. The progress of this therapy is easily monitored by conventional techniques and assays.

The antibody composition may be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the antibody to be administered will be governed by such considerations, and is the minimum amount necessary to prevent, ameliorate, or treat the HMW-MAA mediated disease, condition or disorder, including treating various HMW-MAA mediated diseases, conditions and disorders, particularly to treat HMW-MAA expressing cancer cells, and most particularly to treat tumor cell metastases. Such amount may be preferably below the amount that is toxic to the host or renders the host significantly more susceptible to infections.

The antibody need not be, but may optionally formulated with one or more agents currently used to prevent or treat the disorder in question. For example, in cancer, the antibody may be given in conjunction with chemo therapeutic agent or in ADEPT as described above. The effective amount of such other agents depends on the amount of anti-HMW-MAA antibody present in the formulation, the type of disease, condition or disorder or treatment, and other factors discussed above. These are generally used in similar dosages and administration routes as described herein.

G. Articles of Manufacture

Articles of manufacture containing materials useful for the treatment of the diseases, disorders or conditions described above are provided, including for treatment of cancer. The article of manufacture may comprise a container and a label. Suitable containers include, for example, bottles, vials, syringes, and test tubes. The containers may be formed from a variety of materials such as glass or plastic. The container may hold a composition which is effective for treating the condition and may have a sterile access port (for example the container may be an intravenous solution bag or a vial having a stopper pierceable by a hypodermic injection needle). The active agent in the composition may be the anti-HMW-MAA antibody. The label on, or associated with, the container indicates that the composition may be used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

This disclosure is further illustrated by the following examples which are provided to facilitate the practice of the disclosed methods. These examples are not intended to limit the scope of the disclosure in any way.

EXAMPLES

Example 1

Cloning and Human-Engineering of IND-1 and IND-2

Murine IND-1 and IND-2 monoclonal antibodies may be human engineered by substitution of one or more amino acids in a murine variable region sequence to a corresponding residue in a human variable region sequence, such as an individual human variable region sequence or a consensus variable region sequence.

In an exemplary method, the murine IND-1 and IND-2 light and heavy variable region sequence are aligned to a human light chain and heavy chain variable region sequence, respectively. Such a human variable region sequence can be any human variable region sequence including a consensus sequence based on one or more individual variable region sequences. Next, one or more amino acid residues in the murine sequence are selected for substitution to an amino acid residue in a corresponding human sequence. Amino acid residues for substitution may be one or more residues that are identified as candidates for change in U.S. Pat. No. 5,766,886. The '886 patent identified seventy-three low risk positions in antibody light and heavy chain variable regions (thirty-eight in the light chain variable region and thirty-five in the heavy chain variable region) and twenty-nine moderate risk positions in antibody light and heavy chain variable regions (twelve in the light chain variable region and seventeen in the heavy chain variable region) as being candidates for change. For example, the '886 patent shows low risk positions in the variable regions as circles and moderate risk positions in the variable regions as triangles in the lines labeled "risk" in FIGS. 1A, 1B, 5A, 5B, 6A, 6B, 10A and 10B.

For human-engineering of the murine IND-1 light chain variable region, the IND-1 variable region sequence may be aligned to human sequence (e.g., kappa-4 consensus sequence) and changes may be made at one or more of the 38 low risk amino acid residues. For example, 13 changes may be made at low risk amino acid residues (see, e.g., Table 1, middle row). Additionally or alternatively, changes may be made at one or more of the 12 moderate risk amino acid residues. For example, 18 amino acid changes may be made at low and moderate risk amino acid residues (see, e.g., Table 1, lower row).

For human-engineering of the murine IND-1 heavy chain variable region, the IND-1 variable region may be aligned to a human sequence (e.g., gamma-3 consensus sequence) and changes may be made at one or more of the 35 low risk amino acid residues. For example, 10 changes may be made at low risk amino acid residues (see, e.g., Table 2, middle row). Additionally or alternatively, changes may be made at one or more of the 17 moderate risk amino acid residues. For example, 12 amino acid changes may be made at low and moderate risk amino acid residues (see, e.g., Table 2, lower row).

For human-engineering of the murine IND-2 light chain variable region, the IND-1 variable region sequence may be aligned to human sequence (e.g., kappa-2 consensus sequence) and changes may be made at one or more of the 38 low risk amino acid residues. For example, 15 changes may be made at low risk amino acid residues (see, e.g., Table 3, middle row). Additionally or alternatively, changes may be made at one or more of the 12 moderate risk amino acid residues. For example, 17 amino acid changes may be made at low and moderate risk amino acid residues (see, e.g., Table 3, lower row).

For human-engineering of the murine IND-2 heavy chain variable region, the IND-1 variable region may be aligned to a human sequence (e.g., gamma-3 consensus sequence) and changes may be made at one or more of the 35 low risk amino acid residues. For example, 13 changes may be made at low risk amino acid residues (see, e.g., Table 4, middle row). Additionally or alternatively, changes may be made at one or more of the 17 moderate risk amino acid residues. For example, 20 amino acid changes may be made at low and moderate risk amino acid residues (see, e.g., Table 4, lower row).

The amino acid sequence of the IND-1 and IND-2 mouse variable regions along with the changes in each variable region as a result of the human engineering process are shown in Tables 1 and 2 for IND-1 and Tables 3 and 4 for IND-2.

TABLE 1

Peptide sequence of murine and human-engineered IND-1 light chains.

| V-Region | Amino Acids 1-112 |
|---|---|
| Mouse | DIVMTQSQKFMSTSVGDRVSVTCKASQNVDTNVAWYQQK PGQSPEPLLFSASYRYTGVPDRFTGSGSGTDFTLTISNV QSEDLAEYFCQQYNSYPLTFGGGTKLVIKRA (SEQ ID NO: 1) |
| Human Engin. | DIVMTQSQDSMATSVGERVTVNCKASQNVDTNVAWYQQK PGQSPEPLLFSASYRYTGVPDRFSGSGSGTDFTLTISSV QAEDVAEYFCQQYNSYPLTFGQGTKLEIKRT (SEQ ID NO: 2) |
| Human Engin. | DIVMTQSQDSLATSLGERVTVNCKASQNVDTNVAWYQQK PGQSPKPLLFSASYRESGVPDRFSGSGSGTDFTLTISSV QAEDVAEYFCQQYNSYPLTFGQGTKLEIKRT (SEQ ID NO: 3) |

TABLE 2

Peptide sequence of murine and human-engineered IND-1 heavy chains.

| V-Region | Amino Acids 1-116 |
|---|---|
| Mouse | EVKVEESGGGLVQPGGSMKLSCVVSGFTFSNYWMNWV RQSPEKGLEWIAEIRLKSNNFARYYAESVKGRFTISR DDSKSSVYLQMINLRAEDTGIYYCTSYGNYVGHYFDH WGQGTTLTVSS (SEQ ID NO: 4) |
| Human Engin. | EVQVEVSGGGLVQPGGSMRLSCAVSGFTFSNYWMNWV RQSPEKGLEWIAEIRLKSNNFARYYAESVKGRFTISR DNSKNSLYLQMISLRAEDTAIYYCTSYGNYVGHYFDH WGQGTLLTVSS (SEQ ID NO: 5) |
| Human Engin. | EVQVEVSGGGLVQPGGSMRLSCAVSGFTFSNYWMNWV RQSPGKGLEWIAEIRLKSNNFARYYAESVKGRFTISR DNSKNTLYLQMISLRAEDTAIYYCTSYGNYVGHYFDH WGQGTLLTVSS (SEQ ID NO: 6) |

TABLE 3

Peptide sequence of murine and human-engineered IND-2 light chains.

| V-Region | Amino Acids 1-112 |
|---|---|
| Mouse | DILLTQSPAILSVTPGETVSLSCRASQTIYKNLHWQQ KSHRSPRLLIKYGSDSISGIPSRFTGSGSGTDYTLNIN SVKPEDEGIYYCLQGYSTPWTFGGGTKLEIKRA (SEQ ID NO: 7) |
| Human Engin. | DIVLTQSPSLSVTPGETVSLSCRASQTIYKNLHWYQQK SGQSPRLLIKYGSDRISIGIPDRFSGSGSGTDYTLKIS RVEPEDVGIYYCLQGYSTPWTFGQGTKLEIKRT (SEQ ID NO: 8) |
| Human Engin. | DIVLTQSPLSLSVTPGETVSLSCRASQTIYKNLHWYLQ KSGQSPQLLIKYGSDRISIGIPDRFSGSGSGTDYTLKIS RVEPEDVGIYYCLQGYSTPWTFGQGTKLEIKRT (SEQ ID NO: 9) |

TABLE 4

Peptide sequence of murine and human-engineered IND-2 heavy chains.

| V-Region | Amino Acids 1-112 |
|---|---|
| Mouse | QIQLVQSGPELKKPGETVKISCKASGYTFTDYSMHWVK KTPGKGLKWLGWINTATGEPTYADDFKGRFAISLETSA RTVYLQINNLRNEDTATYFCFSYYDYWGQGTTLTVSS (SEQ ID NO: 10) |
| Human Engin. | QIQLVQSGPEVKKPGESVKISCKASGYTFTDYSMHWVK KAPGQGLKWLGWINTATGEPTYADDFKGRFTITLDTST RTVYLEISSLRSEDTATYFCGSYYDYWGQGTLLTVSS (SEQ ID NO: 11) |
| Human Engin. | QIQLVQSGPEVKKPGESVKISCKASGYTFTDYSMHWVR KAPGQGLEWLGWINTATGEPTYAQKFQGRFTITLDTST STVYLEISSLRSEDTAVYFCFSYYDYWGQGTLLTVSS (SEQ ID NO: 12) |

Example 2

Expression and Evaluation of Human Engineered HMW-MAA Antibodies

Expression plasmids are constructed which contain the human-engineered IND-1 and IND-2 light and heavy chain variable regions configured for expression of Fab (see, e.g., FIG. 1). The expression construct contains the genes to be expressed under control of the *Salmonella typhimurium* araB promoter and the araC gene which controls expression from the araB promoter. The expression plasmid may be transformed into the *E. coli* E104 production strain. Optionally, frozen glycerol research bank cultures may be prepared.

Expression of human-engineered anti-HMW-MAA Fabs may be evaluated by any known method in the art. In an exemplary method, *E. coli* strain E104 is transformed with expression constructs for production of human-engineered anti-HMW-MAA Fabs. The transformed *E. Coli* are grown at 37° C. in TYE broth to an $A_{600}$ of 0.5. The cultures are then induced with 0.1% L-arabinose and incubated for an additional 16-20 hours at 30° C. Next, culture supernatants are evaluated for levels of productivity by ELISA (e.g., precoat Immunolon II plates with a monoclonal antibody against human Fd, detect with anti-human Kappa light chain reagent).

Results indicated that secretion levels of human-engineered Fabs derived from IND-2 and human-engineered Fabs derived from IND-1 were at ~215 ng/ml and at ~390 ng/ml, respectively.

Example 3

Binding Studies

Human engineered anti-HMW-MAA antibodies may be generated and tested for binding affinity compared to the murine IND-1 and IND-2 monoclonal antibodies.

In an exemplary method, the ability of human-engineered anti-HMW-MAA antibodies, as prepared in Example 2, to bind to cells expressing HMW-MAA (e.g., Langenais, SH3, Carlough, SH4, HS936TC1, WM 115, HS69ST, G361, HS294T, Minor, Brown, A375, Loy2, C8161, Gilliam, HS852T, CH5T) may be tested using a competition binding assay with biotinylated murine IND-1 and IND-2. For these studies, the concentrations of biotinylated IND-1 and IND-2 used for the competition studies is established by determining the antibody concentrations needed to saturate binding to cells that express HMW-MAA. For the competition assay, fixed concentrations of the biotinylated antibodies (~70% of saturation) are used in combination with two-fold serial dilutions of the competing antibodies. Bound murine antibodies are then detected with aviden peroxidase.

Figure 2:
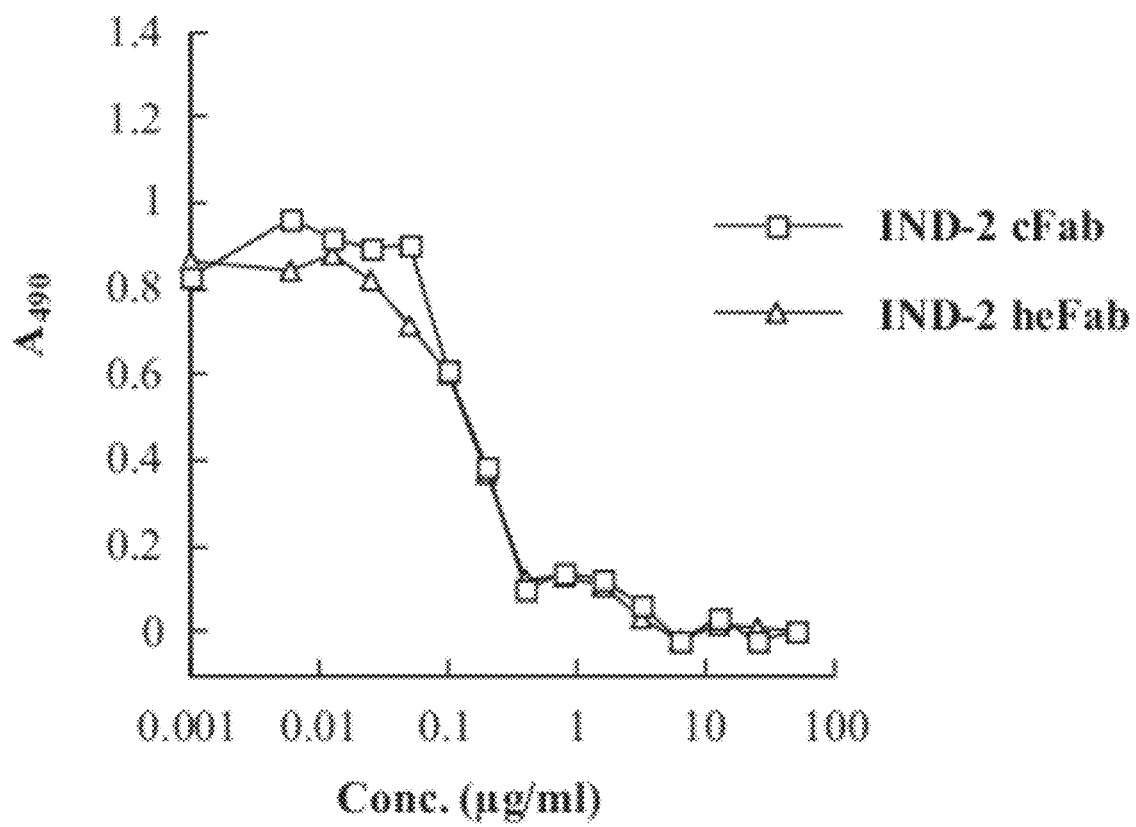
FIG. 2 depicts competition binding studies between human engineered or chimeric IND-2 Fabs and biotinylated murine IND-2 IgG on Minor melanoma cells.

Human-engineered Fabs (derived from IND-2) may be used to compete with the binding of the biotinylated murine IND-2 IgG on cells expressing HMW-MAA. The results demonstrated that Fabs competed in a similar manner with the IgG indicating that the human-engineering did not adversely affect binding of IND-2 antibody to its target (see, e.g., FIG. 2).

Example 4

ADCC Studies with Humanized anti-HMW-MAA Antibodies

Human engineered anti-HMW-MAA Fabs, including those described in Example 1, may be reformatted to an IgG1 isotype and evaluated for theft in vitro activity in ADCC (antibody-dependent cellular cytotoxicity) and CDC (complement dependent cytotoxicity) studies. Reformatted antibodies may be expressed in a transient transfection of 293E cells and isolated for use in in-vitro assays. ADCC and/or CDC assays may be performed on melanoma cells lines that express high levels of HMW-MAA (e.g., Langenais, SH3, Carlough, SH4, HS936TC1, WM 115, HS695T, G361, HS294T, Minor, Brown, A375, Loy2, C8161, Gilliam, HS852T, CH5T). Anti-EpCam (ING-1) and cell lines that express EpCam may be used as a positive control. Tests for ADCC or CDC activity may be conducted by any known method in the art.

In an exemplary ADCC assay, the amount of lactate dehydrogenase released into a media may be used to estimate the number of non-viable cells. Briefly, 20 µl of human engineered antibody (diluted at a 6× concentration) is added to wells in a U-bottom 96 well plate. Next, target cells (e.g., melanoma cells) are filtered through a 70 µm filter to remove cell aggregates and the remaining cells are counted. The appropriate target cell number per well has been determined according to established methods (see, e.g., Promega Cyto-Tox 96® Non-Radioactive Cytotoxicity Assay). 50 µl of target cells are dispensed per well at the appropriate 2× cell density. The wells are then washed one time with PBS and the plate is then centrifuged at 1400 rpm for 5 minutes. Next, the wells resuspended in RPM and 5% human AB serum. This ADCC assay is preformed with peripheral blood mononuclear cells (PBMC) prepared from blood obtained from healthy volunteers as effector cells. PBMCs are detached, counted, and centrifuged at 1400 rpm for 5 minutes. After centrifugation, the cells are resuspended in RPMI+5% AB serum (ABS, Sigma, St. Louis, Mo.). Next, 50 µl PBMCs are dispensed to wells containing target cells and antibody for a final well volume of 120 µl and the plates are briefly centrifuged for 30 seconds at 300 rpm to sink the cells. The plate is then incubated for 4 hours at 37° C. Next, 6 µl of 20% Triton X-100 (final concentration is 1%) is added per well and the plate is then incubated for 45 minutes at 37° C. While the plate is incubating, prealiquoted LDH assay buffer (Promega G1780 kit) is thawed in room temperature water, protected from light. After the incubation, the plate is centrifuged at 1400 rpm for 5 minutes. For the LDH measurement, 50 µl of supernatant from the incubated wells are transferred to an enzymatic assay plate. 50 µl reconstituted substrate mix is then added to the enzymatic assay plate. The enzymatic assay plate is then incubated for 25 minutes at room temperature, protected from light. Last, 50 µl of stop solution is added to each well and the absorbance is then read at 490 nm.

Example 5

In-vivo Studies

Human engineered anti-HMW-MAA antibodies may be evaluated in animals (e.g., humans) for their ability to treat and/or prevent the development of tumors characterized by the expression of HMW-MAA.

in an exemplary method, the human engineered antibodies may be tested for theft ability to treat an animal with a tumor characterized by expression of HMW-MAA. For example, mice may be injected with 1-10 million melanoma cells subcutaneously in the flank. The tumors are allowed to grow to an average of 100-200 mm$^3$. Next, groups of mice (e.g., 10 mice/group) are randomized and treated intraperitoneally two times per week with 10 mg/kg antibody. Tumor growth is monitored over time (e.g., caliper measurements) and experiments are stopped when tumors reach 1000 mm$^3$.

In another exemplary method, the human engineered antibodies may be tested for theft ability to prevent an animal from developing a tumor characterized by the expression of HMW-MAA. For example, groups of SCID mice (e.g., 10 mice/group) may be injected with 10 mg/kg of IND-1, IND-2, or control antibody. The next day, the mice are injected with 1-10 million melanoma cells subcutaneously in the flank. Next, the mice are treated intraperitoneally two times per week with 10 mg/kg antibody. Tumor growth is monitored over time (e.g., caliper measurements) and experiments are stopped when tumors reach 1000 mm$^3$.

While the present disclosure has been described and illustrated herein by references to various specific materials, procedures and examples, it is understood that the disclosure is not restricted to the particular combinations of materials and procedures selected for that purpose. Numerous variations of such details can be implied as will be appreciated by those skilled in the art. It is intended that the specification and examples be considered as exemplary only, with the true scope and spirit of the disclosure being indicated by the following claims. All references, patents, and patent applications referred to in this application are herein incorporated by reference in their entirety.

The invention claimed is:

1. An isolated anti-high molecular weight melanoma associated antigen (HMW-MAA) antibody (anti-HMW-MAA) or antigen binding fragment thereof which binds to human HMW-MAA comprising a light chain variable region comprising the amino acid sequence of SEQ ID NO: 8 or SEQ ID NO: 9 and a heavy chain variable region comprising the amino acid sequence of SEQ ID NO: 11 or SEQ ID NO 12.

2. A conjugate comprising the anti-HMW-MAA antibody or antigen binding fragment thereof of claim 1 bound to a cytotoxic or non-cytotoxic agent.

3. A method for determining the presence of HMW-MAA protein comprising exposing a sample suspected of containing the HMW-MAA protein to the anti-HMW-MAA antibody or antigen binding fragment thereof of claim 1 and detecting binding of the antibody or antigen binding fragment thereof to the sample, wherein the binding of the antibody or antigen binding fragment thereof to the sample is indicative of the presence of HMW-MAA protein in the sample.

4. A kit comprising the anti-HMW-MAA antibody or antigen binding fragment thereof of claim 1 and instructions for using the anti-HMW-MAA antibody or antigen binding fragment thereof to detect the HMW-MAA protein.

5. A composition comprising one or more anti-HMW-MAA antibodies or antigen binding fragments thereof of claim 1 and one or more pharmaceutically acceptable carriers or diluents.

6. The anti-HMW-MAA antibody of claim 1, wherein the antibody is a full length antibody.

7. The anti-HMW-MAA antibody of claim 1, wherein the antibody is a human IgG.

8. The anti-HMW-MAA antibody or antigen binding fragment thereof of claim 1, wherein the antigen binding fragment is a Fab, Fab', Fab'-SH, Fv, scFv, F(ab')₂ or SCA (single chain antibody).

9. A conjugated anti-HMW-MAA antibody or antigen binding fragment thereof of claim 1, wherein the antibody or antigen binding fragment thereof is bound to a detectable label.

10. An immobilized anti-HMW-MAA antibody or antigen binding fragment thereof of claim 1, wherein the antibody or antigen binding fragment thereof is bound to a solid phase.

* * * * *

SEQUENCE LISTING

```
<160> NUMBER OF SEQ ID NOS: 12

<210> SEQ ID NO 1
<211> LENGTH: 109
<212> TYPE: PRT
<213> ORGANISM: Artificial
<220> FEATURE:
<223> OTHER INFORMATION: Synthesized: Murine IND-1 light chain

<400> SEQUENCE: 1

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Leu
                85                  90                  95

Thr Phe Gly Gly Gly Thr Lys Leu Val Ile Lys Arg Ala
            100                 105
```

```
<210> SEQ ID NO 2
<211> LENGTH: 109
<212> TYPE: PRT
<213> ORGANISM: Artificial
<220> FEATURE:
<223> OTHER INFORMATION: Synthesized: Human engineered IND-1 light chain
      1

<400> SEQUENCE: 2

Asp Ile Val Met Thr Gln Ser Gln Asp Ser Met Ala Thr Ser Val Gly
1               5                   10                  15

Glu Arg Val Thr Val Asn Cys Lys Ala Ser Gln Asn Val Asp Thr Asn
            20                  25                  30

Val Ala Trp Tyr Gln Gln Lys Pro Gly Gln Ser Pro Glu Pro Leu Leu
        35                  40                  45

Phe Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Val Gln Ala
65                  70                  75                  80

Glu Asp Val Ala Glu Tyr Phe Cys Gln Gln Tyr Asn Ser Tyr Pro Leu
                85                  90                  95

Thr Phe Gly Gln Gly Thr Lys Leu Glu Ile Lys Arg Thr
            100                 105

<210> SEQ ID NO 3
<211> LENGTH: 109
<212> TYPE: PRT
<213> ORGANISM: Artificial
<220> FEATURE:
<223> OTHER INFORMATION: Synthesized: Human engineered IND-1 light
      chain 2

<400> SEQUENCE: 3

Asp Ile Val Met Thr Gln Ser Gln Asp Ser Leu Ala Thr Ser Leu Gly
1               5                   10                  15

Glu Arg Val Thr Val Asn Cys Lys Ala Ser Gln Asn Val Asp Thr Asn
            20                  25                  30

Val Ala Trp Tyr Gln Gln Lys Pro Gly Gln Ser Pro Lys Pro Leu Leu
        35                  40                  45

Phe Ser Ala Ser Tyr Arg Glu Ser Gly Val Pro Asp Arg Phe Ser Gly
    50                  55                  60

Ser Gly Ser Gly Thr Asp Phe Thr Leu Thr Ile Ser Ser Val Gln Ala
65                  70                  75                  80

Glu Asp Val Ala Glu Tyr Phe Cys Gln Gln Tyr Asn Ser Tyr Pro Leu
                85                  90                  95

Thr Phe Gly Gln Gly Thr Lys Leu Glu Ile Lys Arg Thr
            100                 105

<210> SEQ ID NO 4
<211> LENGTH: 122
<212> TYPE: PRT
<213> ORGANISM: Artificial
<220> FEATURE:
<223> OTHER INFORMATION: Synthesized: Murine IND-1 heavy chain

<400> SEQUENCE: 4

Glu Val Lys Val Glu Glu Ser Gly Gly Gly Leu Val Gln Pro Gly Gly
1               5                   10                  15

Ser Met Lys Leu Ser Cys Val Val Ser Gly Phe Thr Phe Ser Asn Tyr
            20                  25                  30
```

```
Trp Met Asn Trp Val Arg Gln Ser Pro Glu Lys Gly Leu Glu Trp Ile
         35                  40                  45

Ala Glu Ile Arg Leu Lys Ser Asn Asn Phe Ala Arg Tyr Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Ile Asn Leu Arg Ala Glu Asp Thr Gly Ile Tyr
                 85                  90                  95

Tyr Cys Thr Ser Tyr Gly Asn Tyr Val Gly His Tyr Phe Asp His Trp
                100                 105                 110

Gly Gln Gly Thr Thr Leu Thr Val Ser Ser
                115                 120

<210> SEQ ID NO 5
<211> LENGTH: 122
<212> TYPE: PRT
<213> ORGANISM: Artificial
<220> FEATURE:
<223> OTHER INFORMATION: Synthesized: Human engineered IND-1 heavy chain
      1

<400> SEQUENCE: 5

Glu Val Gln Val Glu Val Ser Gly Gly Gly Leu Val Gln Pro Gly Gly
 1               5                  10                  15

Ser Met Arg Leu Ser Cys Ala Val Ser Gly Phe Thr Phe Ser Asn Tyr
                 20                  25                  30

Trp Met Asn Trp Val Arg Gln Ser Pro Glu Lys Gly Leu Glu Trp Ile
         35                  40                  45

Ala Glu Ile Arg Leu Lys Ser Asn Asn Phe Ala Arg Tyr Tyr Ala Glu
 50                  55                  60

Ser Val Lys Gly Arg Phe Thr Ile Ser Arg Asp Asn Ser Lys Asn Ser
 65                  70                  75                  80

Leu Tyr Leu Gln Met Ile Ser Leu Arg Ala Glu Asp Thr Ala Ile Tyr
                 85                  90                  95

Tyr Cys Thr Ser Tyr Gly Asn Tyr Val Gly His Tyr Phe Asp His Trp
                100                 105                 110

Gly Gln Gly Thr Leu Leu Thr Val Ser Ser
                115                 120

<210> SEQ ID NO 6
<211> LENGTH: 122
<212> TYPE: PRT
<213> ORGANISM: Artificial
<220> FEATURE:
<223> OTHER INFORMATION: Synthesized: Human engineered IND-1 heavy chain
      2

<400> SEQUENCE: 6

Glu Val Gln Val Glu Val Ser Gly Gly Gly Leu Val Gln Pro Gly Gly
 1               5                  10                  15

Ser Met Arg Leu Ser Cys Ala Val Ser Gly Phe Thr Phe Ser Asn Tyr
                 20                  25                  30

Trp Met Asn Trp Val Arg Gln Ser Pro Glu Lys Gly Leu Glu Trp Ile
         35                  40                  45

Ala Glu Ile Arg Leu Lys Ser Asn Asn Phe Ala Arg Tyr Tyr Ala Glu
 50                  55                  60

Ser Val Lys Gly Arg Phe Thr Ile Ser Arg Asp Asn Ser Lys Asn Thr
 65                  70                  75                  80
```

```
Leu Tyr Leu Gln Met Ile Ser Leu Arg Ala Glu Asp Thr Ala Ile Tyr
                85                  90                  95

Tyr Cys Thr Ser Tyr Gly Asn Tyr Val Gly His Tyr Phe Asp His Trp
            100                 105                 110

Gly Gln Gly Thr Leu Leu Thr Val Ser Ser
        115                 120

<210> SEQ ID NO 7
<211> LENGTH: 109
<212> TYPE: PRT
<213> ORGANISM: Artificial
<220> FEATURE:
<223> OTHER INFORMATION: Synthesized: Murine IND-2 light chain

<400> SEQUENCE: 7

Asp Ile Leu Leu Thr Gln Ser Pro Ala Ile Leu Ser Val Thr Pro Gly
1               5                   10                  15

Glu Thr Val Ser Leu Ser Cys Arg Ala Ser Gln Thr Ile Tyr Lys Asn
            20                  25                  30

Leu His Trp Tyr Gln Gln Lys Ser His Arg Ser Pro Arg Leu Leu Ile
        35                  40                  45

Lys Tyr Gly Ser Asp Ser Ile Ser Gly Ile Pro Ser Arg Phe Thr Gly
50                  55                  60

Ser Gly Ser Gly Thr Asp Tyr Thr Leu Asn Ile Asn Ser Val Lys Pro
65                  70                  75                  80

Glu Asp Glu Gly Ile Tyr Tyr Cys Leu Gln Gly Tyr Ser Thr Pro Trp
                85                  90                  95

Thr Phe Gly Gly Gly Thr Lys Leu Glu Ile Lys Arg Ala
            100                 105

<210> SEQ ID NO 8
<211> LENGTH: 109
<212> TYPE: PRT
<213> ORGANISM: Artificial
<220> FEATURE:
<223> OTHER INFORMATION: Synthesized: Human engineered IND-2 light chain
      1

<400> SEQUENCE: 8

Asp Ile Val Leu Thr Gln Ser Pro Leu Ser Leu Ser Val Thr Pro Gly
1               5                   10                  15

Glu Thr Val Ser Leu Ser Cys Arg Ala Ser Gln Thr Ile Tyr Lys Asn
            20                  25                  30

Leu His Trp Tyr Gln Gln Lys Ser Gly Gln Ser Pro Arg Leu Leu Ile
        35                  40                  45

Lys Tyr Gly Ser Asp Arg Ile Ser Gly Ile Pro Asp Arg Phe Ser Gly
50                  55                  60

Ser Gly Ser Gly Thr Asp Tyr Thr Leu Lys Ile Ser Arg Val Glu Pro
65                  70                  75                  80

Glu Asp Val Gly Ile Tyr Tyr Cys Leu Gln Gly Tyr Ser Thr Pro Trp
                85                  90                  95

Thr Phe Gly Gln Gly Thr Lys Leu Glu Ile Lys Arg Thr
            100                 105

<210> SEQ ID NO 9
<211> LENGTH: 109
<212> TYPE: PRT
<213> ORGANISM: Artificial
```

```
<220> FEATURE:
<223> OTHER INFORMATION: Synthesized: Human engineered IND-2 light chain
      2

<400> SEQUENCE: 9

Asp Ile Val Leu Thr Gln Ser Pro Leu Ser Leu Ser Val Thr Pro Gly
1               5                   10                  15

Glu Thr Val Ser Leu Ser Cys Arg Ala Ser Gln Thr Ile Tyr Lys Asn
            20                  25                  30

Leu His Trp Tyr Leu Gln Lys Ser Gly Gln Ser Pro Gln Leu Leu Ile
        35                  40                  45

Lys Tyr Gly Ser Asp Arg Ile Ser Gly Ile Pro Asp Arg Phe Ser Gly
50                  55                  60

Ser Gly Ser Gly Thr Asp Tyr Thr Leu Lys Ile Ser Arg Val Glu Pro
65                  70                  75                  80

Glu Asp Val Gly Ile Tyr Tyr Cys Leu Gln Gly Tyr Ser Thr Pro Trp
                85                  90                  95

Thr Phe Gly Gln Gly Thr Lys Leu Glu Ile Lys Arg Thr
            100                 105

<210> SEQ ID NO 10
<211> LENGTH: 113
<212> TYPE: PRT
<213> ORGANISM: Artificial
<220> FEATURE:
<223> OTHER INFORMATION: Synthesized: Murine IND-2 heavy chain

<400> SEQUENCE: 10

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Lys Thr Pro Gly Lys Gly Leu Lys Trp Leu
        35                  40                  45

Gly Trp Ile Asn Thr Ala Thr Gly Glu Pro Thr Tyr Ala Asp Asp Phe
    50                  55                  60

Lys Gly Arg Phe Ala Ile Ser Leu Glu Thr Ser Ala Arg Thr Val Tyr
65                  70                  75                  80

Leu Gln Ile Asn Asn Leu Arg Asn Glu Asp Thr Ala Thr Tyr Phe Cys
                85                  90                  95

Phe Ser Tyr Tyr Asp Tyr Trp Gly Gln Gly Thr Thr Leu Thr Val Ser
            100                 105                 110

Ser

<210> SEQ ID NO 11
<211> LENGTH: 113
<212> TYPE: PRT
<213> ORGANISM: Artificial
<220> FEATURE:
<223> OTHER INFORMATION: Synthesized: Human engineered IND-2 heavy chain
      1

<400> SEQUENCE: 11

Gln Ile Gln Leu Val Gln Ser Gly Pro Glu Val Lys Lys Pro Gly Glu
1               5                   10                  15

Ser Val Lys Ile Ser Cys Lys Ala Ser Gly Tyr Thr Phe Thr Asp Tyr
            20                  25                  30

Ser Met His Trp Val Lys Lys Ala Pro Gly Gln Gly Leu Lys Trp Leu
        35                  40                  45
```

```
Gly Trp Ile Asn Thr Ala Thr Gly Glu Pro Thr Tyr Ala Asp Asp Phe
            50                  55                  60

Lys Gly Arg Phe Thr Ile Thr Leu Asp Thr Ser Thr Arg Thr Val Tyr
 65              70                  75                  80

Leu Glu Ile Ser Ser Leu Arg Ser Glu Asp Thr Ala Thr Tyr Phe Cys
                 85                  90                  95

Phe Ser Tyr Tyr Asp Tyr Trp Gly Gln Gly Thr Leu Leu Thr Val Ser
                100                 105                 110

Ser

<210> SEQ ID NO 12
<211> LENGTH: 113
<212> TYPE: PRT
<213> ORGANISM: Artificial
<220> FEATURE:
<223> OTHER INFORMATION: Synthesized: Human engineered IND-2 heavy chain
      2

<400> SEQUENCE: 12

Gln Ile Gln Leu Val Gln Ser Gly Pro Glu Val Lys Lys Pro Gly Glu
 1               5                  10                  15

Ser Val Lys Ile Ser Cys Lys Ala Ser Gly Tyr Thr Phe Thr Asp Tyr
                 20                  25                  30

Ser Met His Trp Val Arg Lys Ala Pro Gly Gln Gly Leu Glu Trp Leu
             35                  40                  45

Gly Trp Ile Asn Thr Ala Thr Gly Glu Pro Thr Tyr Ala Gln Lys Phe
            50                  55                  60

Gln Gly Arg Phe Thr Ile Thr Leu Asp Thr Ser Thr Ser Thr Val Tyr
 65              70                  75                  80

Leu Glu Ile Ser Ser Leu Arg Ser Glu Asp Thr Ala Val Tyr Phe Cys
                 85                  90                  95

Phe Ser Tyr Tyr Asp Tyr Trp Gly Gln Gly Thr Leu Leu Thr Val Ser
                100                 105                 110

Ser
```